(12) United States Patent
Bomgaars

(10) Patent No.: US 9,352,095 B2
(45) Date of Patent: May 31, 2016

(54) CONTAINER SYSTEM

(71) Applicants: BAXTER INTERNATIONAL INC., Deerfield, IL (US); BAXTER HEALTHCARE SA, Glattpark (Opfikon) (CH)

(72) Inventor: Grant Bomgaars, Kildeer, IL (US)

(73) Assignees: BAXTER INTERNATIONAL, INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 338 days.

(21) Appl. No.: 13/826,685

(22) Filed: Mar. 14, 2013

(65) Prior Publication Data

US 2013/0267903 A1    Oct. 10, 2013

Related U.S. Application Data

(60) Provisional application No. 61/621,028, filed on Apr. 6, 2012.

(51) Int. Cl.
*A61M 5/31* (2006.01)
*A61J 1/20* (2006.01)

(52) U.S. Cl.
CPC .... *A61M 5/31* (2013.01); *A61J 1/20* (2013.01)

(58) Field of Classification Search
CPC .......... A61M 5/162; A61M 5/31; A61M 2005/3114; A61M 2005/3115; A61J 1/20
USPC .......... 604/80, 181, 200, 201, 244, 257
See application file for complete search history.

(56) References Cited

U.S. PATENT DOCUMENTS

| 4,140,117 A | 2/1979 | Buckles et al. |
| 4,237,881 A | 12/1980 | Beigler et al. |
| 4,300,554 A | 11/1981 | Hessberg et al. |

(Continued)

FOREIGN PATENT DOCUMENTS

| EP | 2319477 | 5/2011 |
| JP | H07508439 A | 9/1995 |

(Continued)

OTHER PUBLICATIONS

International Preliminary Report on Patentability, International Application No. PCT/US2013/035282, dated Oct. 7, 2014.

(Continued)

*Primary Examiner* — Theodore Stigell
(74) *Attorney, Agent, or Firm* — Marshall, Gerstein & Borun LLP

(57) ABSTRACT

A container system includes a first container assembly and a delivery device. The first container assembly has an administration port and a medication port. The delivery device is attached to the first container assembly, and includes a housing, a connector, a second container, and a plunger shaft. The housing encloses an interior space with the medication port disposed within the interior space. The connector has at least one cannula defining a first sharp end aligned with the medication port and a second sharp end. The second container has an outlet port aligned with the second sharp end of the at least one cannula and a plunger seal moveable within the second container to force contents of the second container through the port. The plunger shaft assembly has a first end that abuts the plunger seal and a second end connected to a trigger.

18 Claims, 13 Drawing Sheets

(56) References Cited

U.S. PATENT DOCUMENTS

| | | |
|---|---|---|
| 4,435,173 A | 3/1984 | Siposs et al. |
| 4,447,232 A | 5/1984 | Sealfon et al. |
| 4,676,122 A | 6/1987 | Szabo et al. |
| 4,681,566 A | 7/1987 | Fenton, Jr. et al. |
| 4,781,689 A | 11/1988 | Sealfon et al. |
| 5,281,198 A | 1/1994 | Haber et al. |
| 5,385,546 A | 1/1995 | Kriesel et al. |
| 5,779,678 A | 7/1998 | Carter |
| 6,062,429 A | 5/2000 | West et al. |
| 6,641,562 B1 | 11/2003 | Peterson |
| 6,669,668 B1 | 12/2003 | Kleeman et al. |
| 6,837,876 B2 | 1/2005 | Bally et al. |
| 6,994,692 B2 | 2/2006 | Langley et al. |
| 7,066,909 B1 | 6/2006 | Peter et al. |
| 7,470,253 B2 | 12/2008 | Kriesel et al. |
| 7,753,884 B2 | 7/2010 | Gallnbock |
| 7,896,849 B2 * | 3/2011 | Delay ........................ 604/181 |
| 2002/0068896 A1 | 6/2002 | Robinson et al. |
| 2006/0015084 A1 | 1/2006 | Clarke et al. |
| 2010/0191214 A1 | 7/2010 | Hommann |

FOREIGN PATENT DOCUMENTS

| | | |
|---|---|---|
| JP | 2008-521494 A | 6/2008 |
| WO | WO 2004/011064 | 2/2004 |
| WO | WO 2011/077434 | 6/2011 |
| WO | WO-2011/101351 A1 | 8/2011 |

OTHER PUBLICATIONS

International Search Report and Written Opinion, International Application No. PCT/US2013/035282, mailing date Jun. 27, 2013 (9 pp.).

Office Action (English translation), Japanese Patent Application No. 2015-504724, mailed Feb. 24, 2016.

* cited by examiner

CONTAINER SYSTEM

BACKGROUND

The present disclosure relates generally to a container system including a delivery device integral with a first container to permit delivery of a material to a fluid disposed in the first container and admixture therewith, and, in particular, to a container system including a delivery device integral with a first container to permit delivery of a material to a fluid disposed in the first container in a closed system and admixture therewith.

Intravenous (IV) delivery of medical fluids from a container or bag to a patient is a commonplace medical procedure. Oftentimes, a drug or additive must be introduced and admixed with the diluent or parenteral nutritional fluid in the container prior to administration to the patient. The introduction of the drug or additive to the bag is conventionally performed using a needle and syringe to introduce the drug or additive through a medication port of the container. Once the drug or additive is introduced, the container may be shaken to encourage mixing, after which a spike is introduced into an administration port of the bag.

Such a method presents several challenges and disadvantages. To begin, the use of needles creates the potential for needle sticks, both with respect to the healthcare professional introducing the drug or additive to the container and with respect to the bag/container itself. In addition, procedures must be followed to ensure that contaminants are not introduced into the container along with the drug or additive; for example, the medication port may be swabbed with alcohol. These further procedures add time and expense; however, failure to carry out such procedures could result in infection of the patient. Certain drugs (such as oncolytics) are highly toxic, and consequently present additional handling challenges for the healthcare professionals assigned the task of dosing and mixing these drugs in the bags prior to administration to the patient. Other drugs are stored in a lyophilized form, and must be reconstituted prior to introduction, increasing the number of steps needed to introduce the drug in the container prior to administration to the patient.

As set forth in more detail below, the present disclosure sets forth an improved assembly embodying advantageous alternatives to the conventional devices and approaches discussed above.

SUMMARY

According to an aspect of the present disclosure, a container system includes a first container assembly and a delivery device. The first container assembly has an administration port and a medication port. The delivery device is attached to the first container assembly, and includes a housing, a connector, a second container, and a plunger shaft. The housing encloses an interior space with the medication port disposed within the interior space. The connector has at least one cannula defining a first sharp end aligned with the medication port and a second sharp end. The second container has an outlet port aligned with the second sharp end of the at least one cannula and a plunger seal moveable within the second container to force contents of the second container through the port. The plunger shaft assembly has a first end that abuts the plunger seal and a second end connected to a trigger.

According to another aspect of the present disclosure, a container system includes a first container assembly having an administration port and a medication port, and a delivery device attached to the first container. The delivery device includes a housing enclosing an interior space, the medication port disposed within the interior space of the housing, a connector having at least one cannula defining a first sharp end aligned with the medication port, a second sharp end, and a third sharp end, a second container having an outlet port aligned with the second sharp end of the at least one cannula and a plunger seal moveable within the second container to force contents of the second container through the outlet port, and a first plunger shaft assembly having a first end that abuts the plunger seal of the second container and a second end connected to an associated trigger. The delivery device also includes a third container having an outlet port aligned with the third sharp end of the at least one cannula and a plunger seal moveable within the third container to force contents of the third container through the outlet port, and a second plunger shaft assembly having a first end that abuts the plunger seal of the third container and a second end connected to an associated trigger. The connector has a first state wherein the connector couples the second and third containers in fluid communication, and a second state wherein the connector couples the first and second containers in fluid communication. The second plunger shaft assembly has a first storage state, and a second operative state wherein the second plunger shaft assembly applies a force to the plunger seal within the third container to force the contents or a portion of the contents of the third container into the second container upon activation of the associated trigger with the connector in the first state. The first plunger shaft assembly has a first storage state, and a second operative state wherein the first plunger shaft assembly applies a force to the plunger seal within the second container to force the contents or a portion of the contents of the second container into the first container upon activation of the associated trigger with the connector in the second state Additional aspects of the disclosure are defined by the claims of this patent.

BRIEF DESCRIPTION OF THE FIGURES

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION

FIGS. 1-7, 8-17. 18-24, and 25-35 illustrate four embodiments, or four classes of embodiments, of a container system according to the present disclosure. The embodiments include common features, as well as unique features. Even as to the unique features, a certain degree of commonality may exist in general terms, even though the embodiments may diverge as to the details of the general features held in common. Consequently, certain common features will be described initially, before describing the unique features or unique details of each embodiment or class of embodiments. For simplicity, the common features are described relative to the embodiment of FIGS. 1-7, although the features could have been described as to the embodiments of FIGS. 8-17, 18-24, and 25-35 instead.

Figure 1:
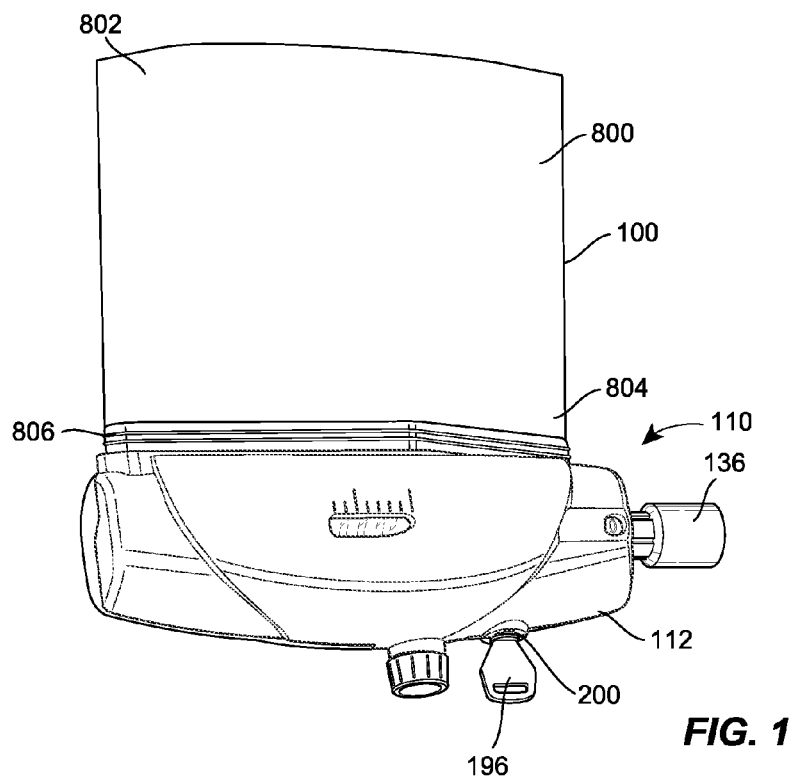
FIG. 1 is a perspective view of a first embodiment of a container system according to the present disclosure.
Figure 2:
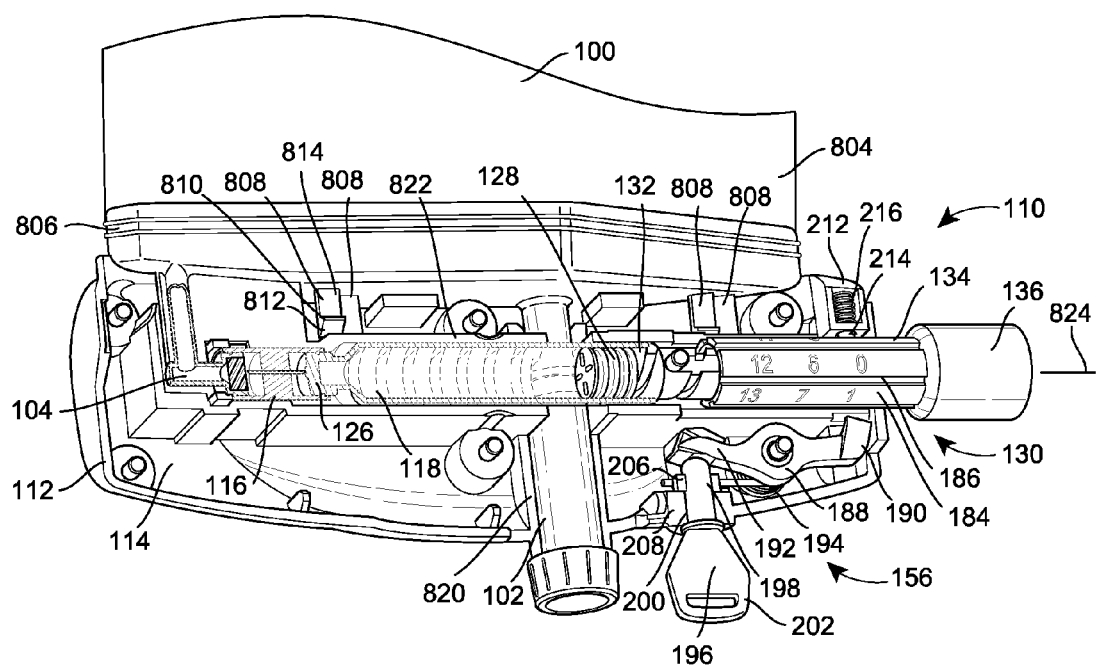
FIG. 2 is a fragmentary, enlarged perspective view of the container system of FIG. 1, with a portion of the housing removed to expose structures of a first container and a delivery device.

Thus, FIGS. 1 and 2 illustrate a container system including a first container 100 and a delivery device 110. The first container 100 has an administration port 102 and a medication port 104 (see FIG. 2). The delivery device 110 is attached to the first container 100 so as to provide a closed system between delivery device 110 and at least the medication port 104 of the first container. The delivery device 110 is used to introduce a drug or additive, for example, to a diluent or a parenteral nutritional fluid in the first container 100 under closed system conditions.

To this end, the delivery device 110 includes a housing 112 enclosing an interior space 114. The medication port 104 is disposed within the interior space 114 of the housing 112. As a consequence, the medication port 104 is not generally accessible. According to certain embodiments, the housing 112 may be sealed about the medication port 104 to prevent contaminants from entering the space 114 about the medication port 104. The housing 112 may even be sealed during the manufacturing process, with the delivery device 110 assembled under clean room conditions so as to limit the likelihood of contaminants being found in the space 114. According to certain embodiments, the housing 112 may include two sections joined together with fasteners, such as screws, although the construction of the housing 112 is not limited to two-part structures or to the use of fasteners, such as screws, but may include other constructions or methods of joining as well.

The delivery device 110 may also include a connector 116 and a second container 118 (which may be referred to as a cartridge, as illustrated), both also disposed within the housing 112 (and in certain embodiments, sealed within the housing 112) as illustrated. It will be recognized, however, that at least a portion of the second container 118 may be disposed outside the housing 112 according to other embodiments. The connector 116 has a cannula 120 (see FIG. 3) with a first sharp end 122 aligned with the medication port 104 and a second sharp end 124. The second container 118 has an outlet port 126 aligned with the second sharp end 124 of the cannula 120 and a plunger seal 128 moveable within the second container 118 to force contents of the second container 118 through the port 126.

As illustrated, the connector 116 may also include a plug 121 from which a first collar or cylindrical wall 123 depends in the direction of the medication port 104, and a second collar or cylindrical wall 125 depends in the direction of the container 118. The cannula 120 may be disposed through the plug 121 such that first collar 123 is disposed about the first sharp end 122 and the second collar 125 is disposed about the second sharp end 124. As illustrated, the first and second collars 123, 125 have approximately the same inner and outer diameter, although this need not be the case according to all embodiments.

In certain embodiments, the medication port 104 may be disposed within the first collar 123 and an end of the container 118 (e.g., outlet port 126) may be disposed within the second collar 125 so as to form a sterile barrier at either end of the connector 116, thus defining a sterile environment within the interior of the connector 116. For example, the medication port 104 may be bonded to the first collar 114, and the end of the container 118 and the second collar 125 fitted within particular tolerances so as to maintain sterility. It will be recognized that other mechanism and methods for forming a sterile barrier at either end of the connector 116 may be used as well.

The delivery device 110 (for example, that illustrated in FIG. 2) may further include a plunger shaft assembly 130 having a first end 132 that abuts the plunger seal 128 and a second end 134 connected to a trigger 136. A force may be applied to the trigger 136, and as a consequence to the plunger shaft assembly 130, to move the plunger shaft assembly 130 against the plunger seal 128 to urge the outlet port 126 of the second container 118 against the second sharp end 124, and sequentially or concurrently to urge the first sharp end 122 against the medication port 104. As a consequence, fluid communication is established between the outlet port 126 and the medication port 104. According to other embodiments (not illustrated), a force applied to the trigger 136 may cause actuation of an automated system, device or drive that causes movement of the plunger shaft assembly 130, with consequential movement of the container 118 relative to the connector 116, and the movement of the container 118 and connector 116 relative to the medication port 104.

The connector 116 may have a storage state wherein the first end 122 is not in fluid communication with the medication port 104 and the second end 124 is not in fluid communication with the outlet port 126. In the storage state, the first end 122 may be spaced from, abutting or only partially inserted into a plug that defines, in part, the medication port 104. Similarly, the second end 124 may be spaced from, abutting or only partially inserted into a stopper of the second container 118 that defines, in part, the outlet port 126. In this fashion, the first sharp end 122 of the connector 116 is not disposed through the plug and the second sharp end 124 of the connector 116 is not disposed through the stopper in the storage state. It will be recognized that an embodiment with the ends 122, 124 partially inserted may advantageously control for potential leaks if one end 122, 124 punctures the corresponding port prematurely, and for sterility or added sterility by shielding the end 122, 124 upon partial insertion into the port (which may occur under the sterile conditions described above).

The connector 116 may also have an operational or operative state wherein the first end 122 is in fluid communication with the medication port 104 and the second end 124 is in fluid communication with the outlet port 126. In such a state, both the first end 122 and the second end 124 may be disposed through the plug of the medication port 104 and the stopper of the second container 118, respectively. The connector 116 may be moved from the storage state to the operational state through the movement of plunger shaft assembly 130 against the plunger seal 128, as illustrated, although the plunger shaft assembly 130 may act against other features of the second container 118 in addition or instead of the plunger seal 128.

According to certain illustrated embodiments of the container system, the plunger shaft assembly 130 may be configured to permit a dose of the drug or additive in the second container 118 to be selected and delivered to the first container 100. According to other illustrated embodiments, the plunger shaft assembly 130 may be configured to guide the user through the steps necessary to reconstitute a lyophilized drug in the second container 118, for example, and then to deliver the reconstituted drug to the first container 100 for admixture with the diluent found therein. The embodiments of the container system according to each such embodiment are described below, with common features identified with common numerals.

Such it is that an embodiment of the container system according to the first class of embodiments, wherein an adjustable dosage is provided, is illustrated in FIGS. 1-7. As explained above, the container system includes the first container 100 with the administration port 102 and the medication port 104. The system also includes the delivery device 110 with the housing 112, the connector 116, the second container 118, and the plunger shaft assembly. For purposes of differentiation, this plunger shaft assembly will be referred to as an adjustable plunger shaft assembly 150, or adjustable assembly 150 for short, in FIGS. 3-7.

Figure 3:
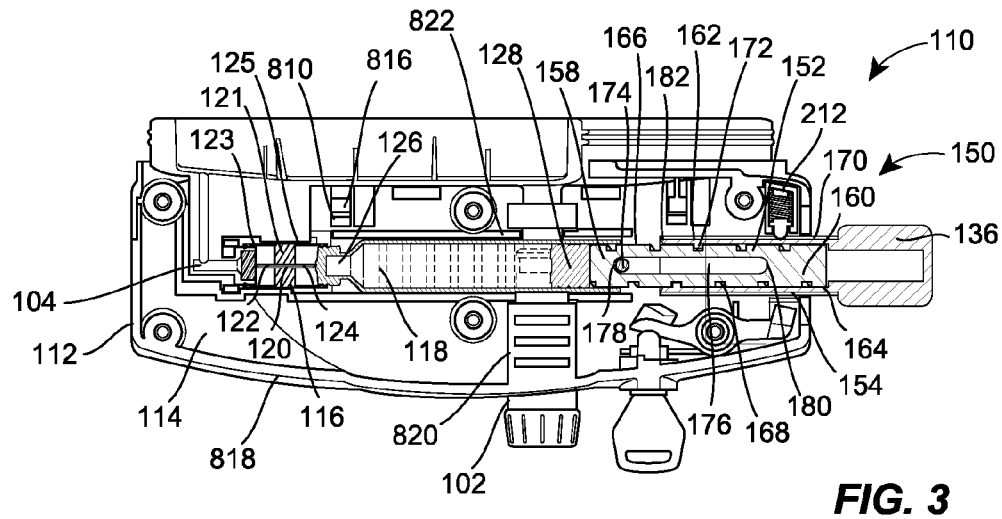
FIG. 3 is a cross-sectional view of the container system of FIG. 1 with a adjustable plunger shaft assembly in a first (zero-dose) state, and a lock in a first, unlocked state.

Turning first to FIG. 3, the adjustable assembly 150 includes first and second shaft sections 152, 154. In general terms, the first shaft section 152 defines the first end 132 of the plunger shaft assembly (compare FIGS. 2 and 3) and the second shaft section 154 defines the second end 134 of the plunger shaft assembly (again, compare FIGS. 2 and 3). The first and second shaft sections 152, 154 are moveable relative to each other to vary a distance between the first and second ends 132, 134 of the plunger shaft assembly.

The adjustable assembly also includes a lock 156 connected to the first and second shaft sections 152, 154 (see FIG. 2). The lock 156 has a first state that permits relative motion between the first and second shaft sections 152, 154. The lock 156 also has a second state that limits relative motion between the first and second shaft sections 152, 154.

In the particular embodiment illustrated in FIGS. 3-7, the first shaft section 152 may be a solid shaft with a first end 158 that defines the first end 132 of the plunger shaft assembly (compare FIGS. 2 and 3) and a second end 160. The second shaft section 154 may be a hollow tube with a first end 162 and a second end 164 that defines the second end 134 of the plunger shaft assembly (compare FIGS. 2 and 3). The second end 160 of the solid shaft 152 and the first end 162 of the hollow tube 154 may threadedly engage each other to permit relative motion thereof.

With reference to FIG. 3, the shaft 152 may have an exterior surface 166 with a groove 168 formed therein, and the tube 154 may have an interior surface 170 with a thread 172 depending therefrom. The thread 172 of the tube 154 may be disposed within the groove 168 of the shaft 152 so as to threadingly engage shaft 152 and tube 154. It will be recognized that a similar threaded engagement could be provided by having the groove formed on the interior surface 170 of the tube 154 and the thread depending from the exterior surface 166 of the shaft 152. It will also be recognized that other mechanisms may be provided to provide relative motion between the first and second shaft section 152, 154.

As illustrated, the adjustable assembly 150 may also include a pin 174 disposed in a slot 176 formed in the solid shaft 152. The pin 174 is secured at its ends to the housing 112, and thus is immovable relative to the housing 112. Despite this, the pin 174 may be described herein as moving relative to features of the adjustable assembly 150, even though the adjustable assembly 150 is, in fact, moving relative to the housing 112 and the pin 174.

The pin 174 cooperates with the slot 176 to resist rotational motion of the solid shaft 152. The pin 174 is generally moveable in the slot 176 between ends 178, 180 of the slot 176, further limited by the general spatial relationship between the shaft 152 and the tube 154. Specifically, the tube 154 has an edge 182 that may overlie the slot 176; the exact position of the edge 182 relative to the slot 176 (particularly, relative to the first and second ends 178, 180 of the slot 176) determines the extent of the relative motion between the shaft 152 and tube 154. The pin 174 is thus moveable relative to the ends 178, 180 unless the edge 182 is disposed between the ends 178, 180, in which case the pin 174 is moveable between the end 178 and the edge 182, although the pin 174 may or may not come in contact with the ends 178, 180 or edge 182. The extent to which the pin 174 is moveable between the ends 178, 180 determines the dose of the contents of the second container 118 delivered to the first container 100.

The spatial relationship between the first and second shaft sections 152, 154 may be limited, or even fixed, through the lock 156. As illustrated, the tube 154 has an exterior surface 184 with a plurality of longitudinal grooves 186 (see FIG. 2). The lock 156 engages the longitudinal grooves 186 to limit relative motion between the solid shaft 152 and hollow tube 154.

According to an embodiment of the lock 156 illustrated in FIGS. 2-7 and best seen in FIG. 2, the lock 156 includes a lever 188 having a first end 190 and a second end 192. The lock 156 also includes a spring 194 that biases the first end 190 toward one of the plurality of longitudinal grooves 186. The lock 156 also includes a key 196 that abuts the second end 192 of the lever 188 when inserted into the lock 156 to space the first end 190 of the lever 188 from the plurality of longitudinal grooves 186.

In particular, the key 196 has a shaft 198 is disposed through an opening 200 in housing 112 of the delivery device 110, and a head 202 that is manipulatable by the user. The shaft 198 has an end with a pair of supports 206 spaced from the end. The supports 206 abut against an inner surface or shoulder 208 formed at an inner end of the opening 200 in the housing 112. The cooperation of the supports 206 with the shoulder 208 ensures that the shaft 198 cooperates with the second end 192 of the lever 188 to space the first end 190 of the lever from the grooves 186 to limit the cooperation of the end 190 and the grooves 186 (i.e., to prevent the first end 190 of the lever 188 from being received in the grooves 186). To accommodate the supports 206, which depend radially outwardly from the shaft 198, the opening 200 may have a complementary cross-section.

As also seen in FIGS. 2 and 3, on the opposite side of the adjustable assembly 150 from the first end 190 of the lever 188 is a detent 212. The detent 212 may be received in one of the grooves 186 to provide an audible and/or tactile indication of the relative rotational movement of the first and second shaft sections 152, 154. The detent 212 may include a ball or other detent feature 214 and a biasing element or spring 216 that urges the detent feature 214 into engagement with one of the grooves 186 (or the surface 184 of the tube 154 between the grooves 186).

The operation of the device is now discussed with reference to FIGS. 2-7. In the first, storage state illustrated in FIGS. 2 and 3, the key 196 is received within the opening 200 in the housing to place the lock 156 in an unlocked state, and the two sections 152, 154 of the adjustable assembly 150 may be disposed in a first, zero-dose state. Because the lock is unlocked, the two sections 152, 154 of the adjustable assembly 150 may be moved relative to each other. However, with the adjustable assembly 150 in the zero-dose state, actuation of the trigger 136 will cause no motion of the plunger seal 128 such that drug will be dispensed, although movement of the trigger 136 may cause the container 118 to advance such that the sharp end 124 of the cannula 120 punctures and then passes through the port 126.

Figure 4:
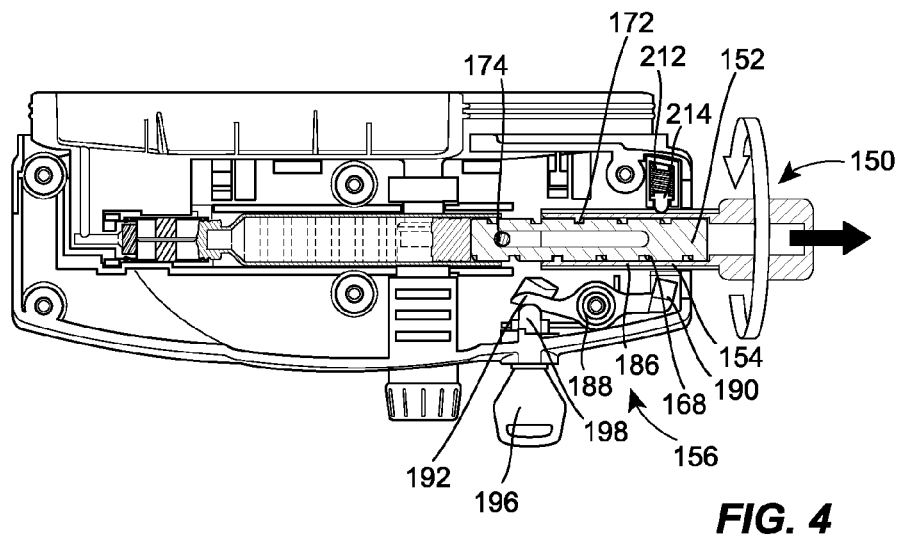
FIG. 4 is a cross-sectional view of the container system of FIG. 1 with the adjustable plunger shaft assembly in a second (non-zero-dose) state, and the lock in the unlocked state.

In FIG. 4, the second shaft section 154 has been moved relative to the first shaft section 152 such that the adjustable assembly 150 is no longer in the zero-dose state. According to the illustrated embodiment, because the first and second shaft sections 152, 154 are connected to each other through a threaded engagement defined by the grooves 168 and the thread 172, the second shaft section 154 is rotated relative to the first shaft section 152 to achieve the relative motion between the two sections 152, 154. As mentioned previously, the pin 174 limits or resists rotational motion of the first shaft section 152 at the same time. The cooperation between the detent 212 (and in particular the detent feature 214) and the grooves 186 provides a tactile and/or audible indication of the rotation of the second shaft section 154. In addition, the second shaft section 154 may have indicia (e.g., numbers) disposed on the exterior surface 184 (see FIG. 2) that are viewable through a window in the housing 112 (see FIG. 1) so that a visual indication of the dose associated with the relative position of the first and second shaft sections 152, 154 may be displayed to the user.

Figure 5:
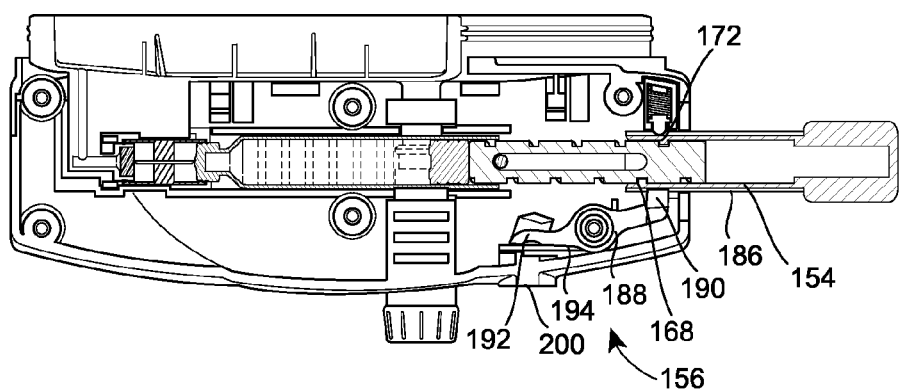
FIG. 5 is a cross-sectional view of the container system of FIG. 1 with the adjustable plunger shaft assembly in the second (non-zero-dose) state, and the lock in a locked state.

Because the shaft 198 of the key 196 abuts against the second end 192 of the lock 156, the first end 190 of the lever 188 is not disposed in the grooves 186 of the second shaft section 154. As a consequence, the second shaft section 154 may be moved relative to the first shaft section 152, as illustrated in FIGS. 4 and 5. However, when the first and second shaft sections 152, 154 of the adjustable assembly 150 have been adjusted to provide the desired dose, the healthcare profession (e.g., a pharmacist or pharmacy employee) removes the key 196 from the lock 156 (see FIG. 5). As a consequence, the biasing force provided by the spring 194 causes the first end 190 of the lever 188 to be urged toward the grooves 186. With the first end 190 disposed in one of the grooves 186, the movement of the second shaft section 154 about its longitudinal axis is resisted or limited.

Figure 6:
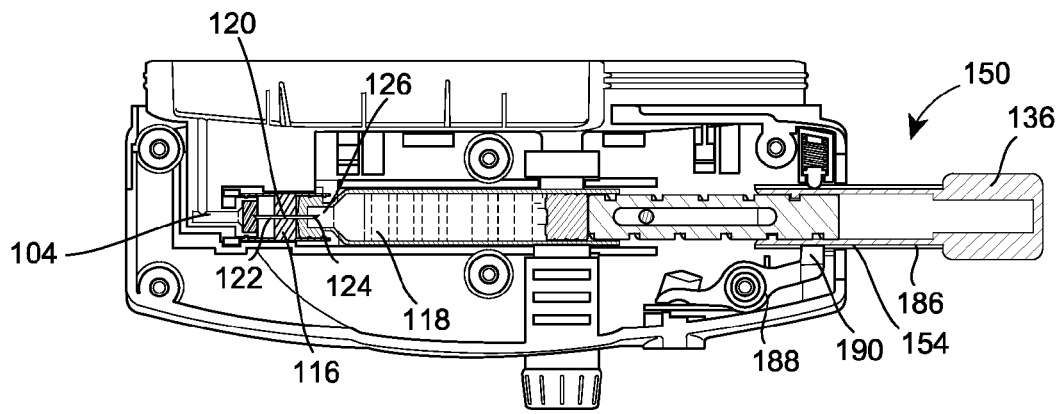
FIG. 6 is a cross-sectional view of the container system of FIG. 1 with the adjustable plunger shaft assembly advanced in the direction of a medication port to open fluid communication between a connector and a second container.
Figure 7:
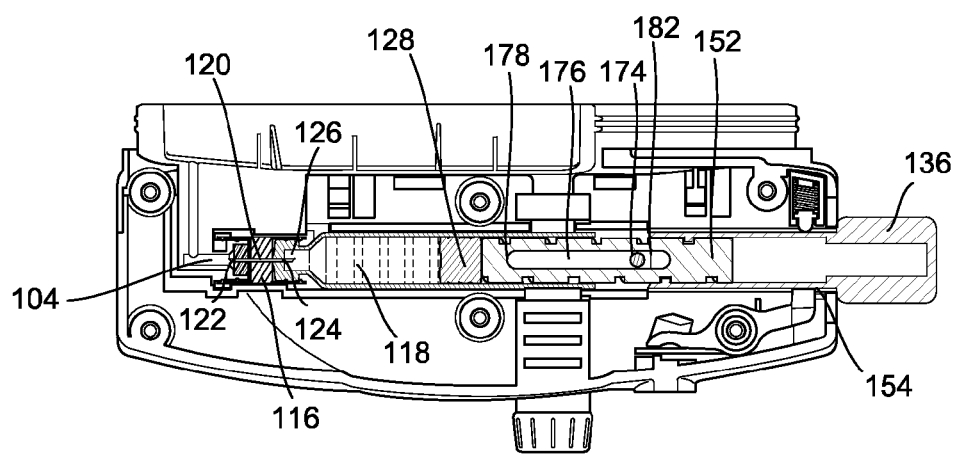
FIG. 7 is a cross-sectional view of the container system of FIG. 1 with the adjustable plunger shaft assembly advanced in the direction of the medication port to open fluid communication between the connector and a medication port of the first container.

At this point, a force may be applied to the trigger 136 to urge the adjustable assembly 150 to the left, as illustrated in FIG. 6. While the cooperation of the lever 188 and the grooves 186 resists rotational motion of the second shaft section 154, the axial movement of the second shaft section 154 (and the remainder of the adjustable assembly 150) is not resisted by the grooves 186 and the lever 188. As the adjustable assembly 150 is moves to the left, the second container 118 is also moved to the left. In fact, the outlet port 126 is moved in the direction of the connector 116 until the second sharp end 124 of the cannula 120 punctures and then passes through the outlet port 126. The cannula 120 is thus placed in fluid communication with the second container 118. Further motion eventually causes the outlet port 126 of the second container 118 to abut against an interior surface of the connector 116, at which point further motion of the second container 118 translates into motion of the connector 116 as well.

Motion of the second container 118 and the connector 116 to the left causes the first sharp end 122 of the cannula 120 to abut against a plug that defines, in part, the medication port 104 of the first container 100. With further axial motion along the common axis of the port 104, connector 116, second container 118 and adjustable assembly 150, the first sharp end 122 punctures and passes through the plug of the medication port 104, thus placing the cannula 120 in fluid communication with the medication port 104. As a further consequence, the second container 118 is in fluid communication with the medication port 104 via the connector 116 (and in particular via the cannula 120).

With still further application of force to the trigger 136 to the left, the adjustable assembly 150 causes the plunger seal 128 to move along the second container 118 in the direction of a first end of the container 118 from a second end of the container 118. The motion of the plunger seal 128 to the left causes the contents of the second container 118 to be ejected from the second container 118 into the cannula, and through the cannula into the medication port 104 and ultimately the first container 100. The amount or volume of material (e.g., drug, additive, etc.) ejected from the second container 118 into the first container 100 will depend on the motion of the second shaft section 154 relative to the first shaft section 152, which motion causes the edge 182 of the second shaft section 154 to be moved relative to the first end 178 of the slot 176, thereby determining the relative motion permitted through the cooperation of the pin 174 and the slot 176 (or at least that portion of the slot 176 defined between the end 178 and the edge 182). The movement of the plunger seal 128 may be visualized through a window in the housing 112, permitting confirmation of the delivery and dose of the material from the second container 118 to the first container 100.

With the drug, additive, or other material thus introduced into the container 100, the container 100 may be shaken to encourage admixture, and then the administration port 102 may be spiked to administer the contents of the container 100 to a patient. To spike the administration port 102, it may be necessary to first remove a cap connected to the administration port 102, as illustrated.

Having thus described the structure and operation of the embodiment illustrated in FIGS. 1-7, another embodiment of the container system according to the second class of embodiments, wherein reconstitution capability is provided, is illustrated in FIGS. 8-17. As was the case with the embodiment illustrated in FIGS. 1-7, the container system of FIGS. 8-17 includes a first container 100 with an administration port 102 and a medication port 104 (see FIG. 9). The system also includes a delivery device 110 with a housing 112, a connector 116, a second container 118, and a plunger shaft assembly (see also FIG. 9). For purposes of differentiation, this plunger shaft assembly will be referred to as a plunger shaft assembly 250.

Figure 8:
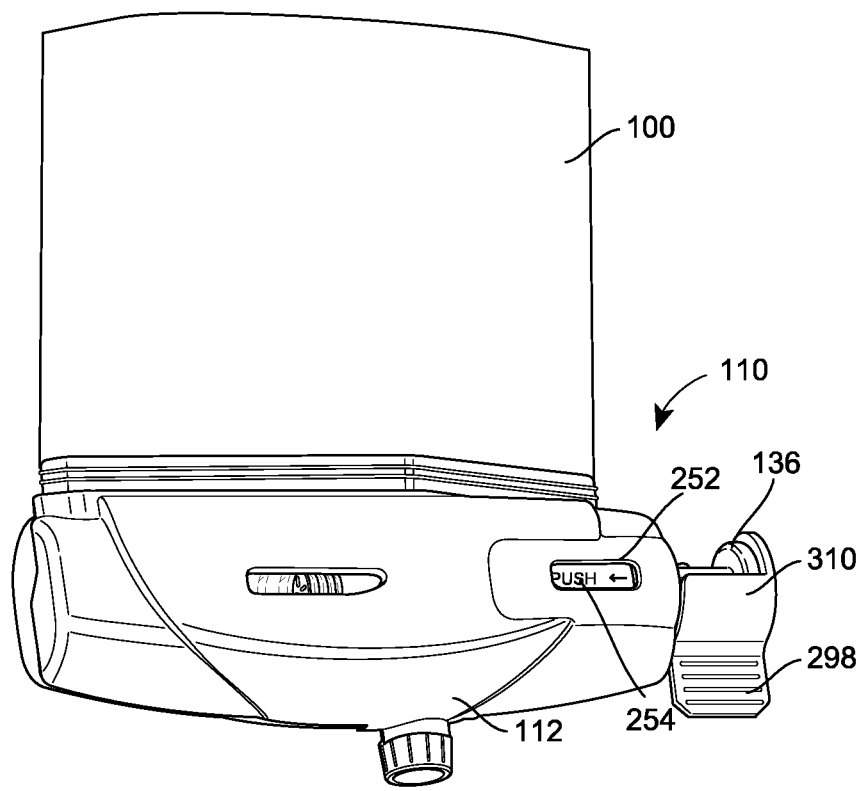
FIG. 8 is a perspective view of a second embodiment of a container system according to the present disclosure.
Figure 9:
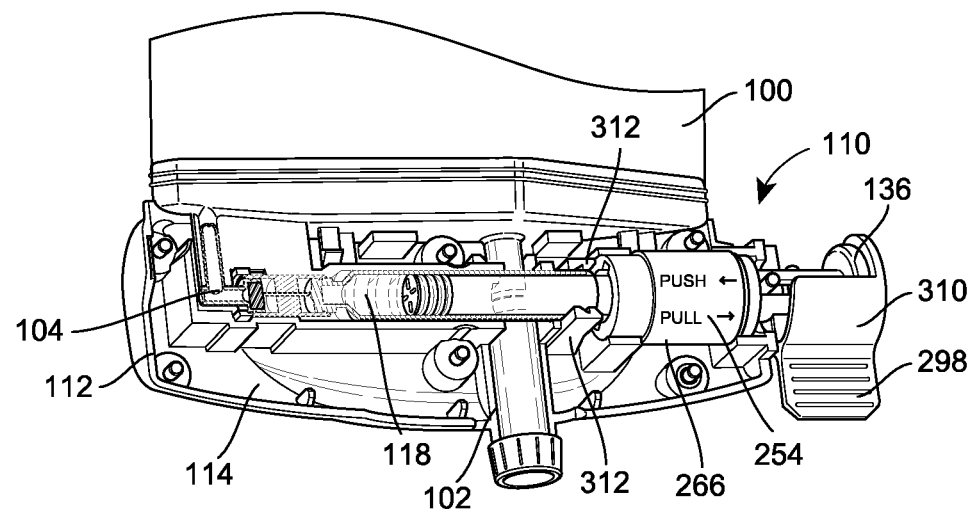
FIG. 9 is a fragmentary, enlarged perspective view of the container system of FIG. 8, with a portion of the housing removed to expose structures of a first container and a delivery device.

According to this embodiment, the housing 112 has a window 252 to permit visualization of a state indicator 254 (compare FIGS. 8 and 9). The state indicator 254 provides visual cues to the user as to the proper use of the plunger shaft assembly 250. The cues may be in the form of an alphanumeric message, a symbolic message, or a combination thereof. According to the illustrated embodiment, the message is a combination or series of simple words (e.g., "PUSH," "PULL," "PUSH," and "SPIKE") as well as symbols (e.g., arrows pointing to the left or right).

Figure 10:
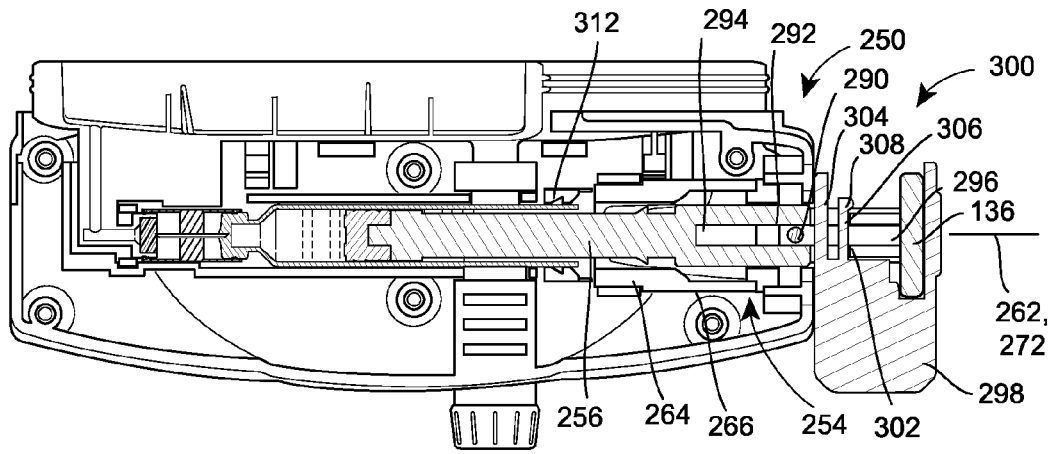
FIG. 10 is a cross-sectional view of the container system of FIG. 1 with a safety lock connected to a plunger shaft assembly.
Figure 11:
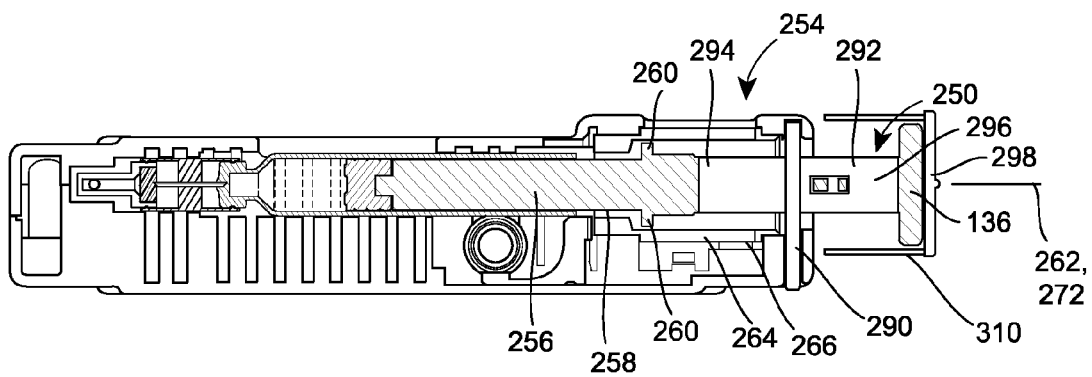
FIG. 11 is a cross-sectional view of the container system of FIG. 1 in a plane orthogonal to that of FIG. 10.
Figure 12:
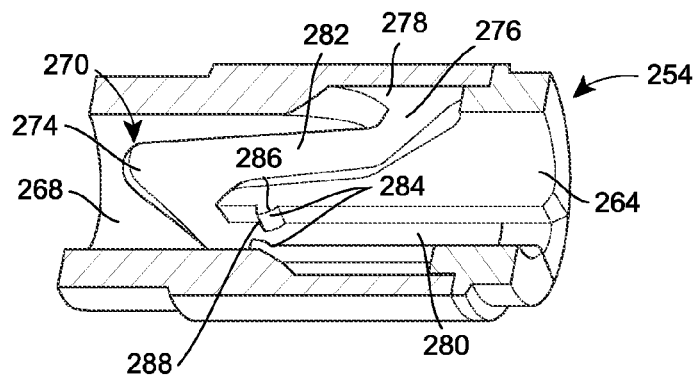
FIG. 12 is an enlarged, cross-sectional view of an indicator assembly according to the present disclosure, exposing a portion of a path disposed on an inner surface of the indicator assembly.

Turning now to FIGS. 10 and 11, the plunger shaft assembly 250 includes a shaft 256 having an exterior surface 258 from which a tab(s) 260 depends (see FIG. 11) and a longitudinal axis 262. The state indicator 254 includes a collar 264 disposed about the plunger shaft assembly 250. The collar 264 has an exterior surface 266 (compare FIGS. 9-11) visible through the window 252 and on which the previously mentioned visual cues may be disposed. As best seen in FIG. 12, the collar 264 also has an interior surface 268 with a path 270 formed therein. The tab(s) 260 is/are disposed within the path 270 and follows the path 270 to cause the collar 264 to rotate about its axis 272 (which is collinear with the longitudinal axis 262) so as to index the visual cues disposed on the exterior surface 266 of the collar 264 in the window 252.

Figure 13:
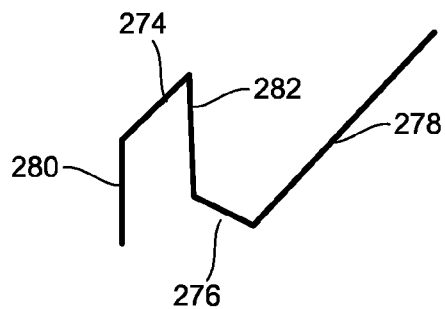
FIG. 13 is a schematic diagram of the path disposed on the inner surface of the indicator assembly.

As seen at least in part in FIG. 12 and represented schematically in FIG. 13, the path 270 has at least first, second and third sections 274, 276, 278 each at an angle to the longitudinal axis 262 of the shaft 256. Because of the desired motion for the plunger shaft assembly 250, the first and third sections 274, 278 have an opposite slope to the second section 276 so that the visual cues will index in the window 252 even though the motion of the plunger shaft assembly 250 is reversed (i.e., a push followed by a pull, followed by another push, before displaying the cue to spike the administration port 102.)

The path 270 may also include fourth and fifth sections 280, 282, each parallel to the longitudinal axis 262. These sections of the path 280, 282 permit the visual cues to be displayed for the motion of the plunger shaft assembly 250 along the first "push" and the "pull" stroke of the plunger shaft assembly 250. Consequently, the fourth section 282 is disposed prior to the first section 274 and the fifth section 282 disposed between the first and second sections 274, 276.

As illustrated in FIG. 12, a pair of inwardly directed blocks 284 is provided near the junction between the first and fourth sections 274, 280 to limit the movement of the tab 260 from the first section 274 back along the fourth section 280. To this end, the blocks have a curved surface 286 on a side of the blocks 284 facing the fourth section 280, and a flat surface 288 perpendicularly oriented to the fourth section 280 on a side of the blocks 284 facing the first section 278. According to certain embodiments, the blocks 284 do not fully prevent the movement of the tab 260 from the first section 274 back along the fourth section 280, but require a sizable force before such motion can occur. Consequently, the blocks 284 still limit the movement of the tab 260, and provide a tactile indicator that such movement is incorrect.

Returning to FIGS. 10 and 11, to resist the inclination of the cooperation of the plunger shaft assembly 250 and the collar 264 to cause rotation of the shaft 256, the plunger shaft assembly 250 also includes a pin 290 disposed in a slot 292 formed in the shaft 256. The pin 290 is disposed in the slot 292 and as the shaft 256 moves axially along the longitudinal axis 262, the pin 290 may be described as moving between first and second ends 294, 296 of the slot 292. The cooperation between the pin 290 and the slot 292 also determines the distance of the movement of the plunger seal 128 in the second container 118.

In addition, the embodiment of the delivery device 110 illustrated in FIGS. 8-17 includes a safety lock 298 (see FIGS. 8-11). The safety lock 298 is connected to the plunger shaft assembly 250 to limit movement of the plunger shaft assembly 250. To this end, the safety lock 298 has a connector 300 disposed in a second slot 302 formed in the shaft 256, as best seen in FIG. 10. For example, the connector 300 may include first and second arms 304, 306 that are disposed in the slot 302, the first arm 304 abutting the housing 112 and the second arm 306 spaced from the first arm 304 and having a hook 308 attached thereto and depending from the arm 306 in a direction parallel to the longitudinal axis 262 of the shaft 256 to resist removal of the connector 300 from the slot 302.

The safety lock 298, as illustrated, also includes a shroud 310 (see FIGS. 8, 9, and 11) that at least partially surrounds the trigger 136 to limit access thereto unless the safety lock 298 is removed. The shroud 310 thus provides a visual indication to the user that the safety lock 298 must be disengaged from the shaft 256 before the plunger shaft assembly 250 may be moved. The shroud 310 also provides a stabilizing function to limit premature removal or separation of the connector 300 from the slot 302 in the shaft 256.

The operation of the embodiment of FIGS. 8-17 is now discussed principally with respect to FIGS. 10 and 12-17. The safety lock 298 first must be disengaged from the shaft assembly 250. Unless the safety lock 298 is removed, the trigger 136 cannot be moved to the left, as illustrated, because of the cooperation between the arm 304 and the housing 112 of the delivery device 110, for example. Moreover, the safety lock 298, and in particular the shroud 310, prevents the trigger 136 from being grasped. The safety lock 298 is disengaged by applying a downward force to pull the arms 304, 306 out of the slot 302 (as viewed in FIG. 10).

Figure 14:
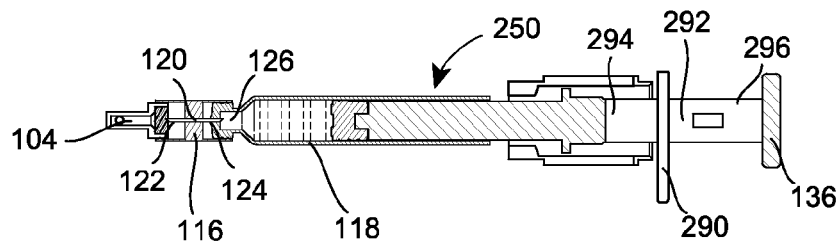
FIG. 14 is a cross-sectional view of the medication port, connector, second container and plunger shaft assembly with the connector in fluid communication with the second connector.

Once the safety lock 298 has been disengaged, a force may be applied to the trigger 136 to move the shaft assembly 250 to the left, as suggested by the indicia on the state indicator 254 as displayed in the window 252 (see, e.g., FIG. 8, "PUSH" with an arrow pointing to the left). With the force thus applied, the shaft assembly 250 transmits a force to the second container 118 to move the second container 118 to the left. As illustrated in FIG. 14, movement of the second container 118 to the left initially causes the second sharp end 124 of the connector 116 to puncture and then pass through the outlet port 126 of the second container 118, thus placing the cannula 120 in fluid communication with the second container 118.

At the same time, the tabs 260 disposed on the exterior surface 258 of the shaft 256 move along the path 270 formed on in the interior surface 268 of the state indicator 254, specifically the collar 264. As noted in FIGS. 12 and 13, the tabs 260 will initially pass along a straight section 280 before coming to a pair of blocks 284. With the application of sufficient force, the tabs 260 will move past the blocks 284, and the curved surfaces 286 of the blocks 284, before coming to the first angled section 274.

Figure 15:
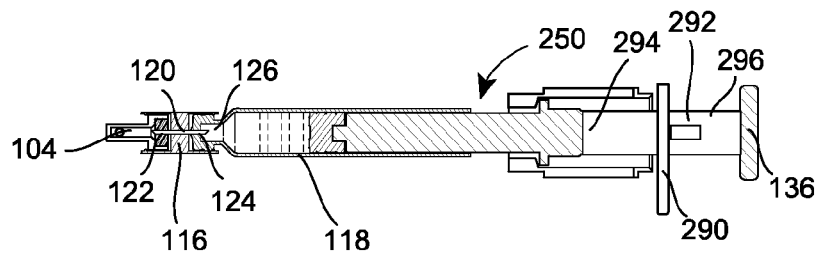
FIG. 15 is a cross-sectional view similar to FIG. 14, with the connector in fluid communication with the medication port and the second container, and the plunger shaft assembly advanced into the second container in the direction of the medication port.
Figure 16:
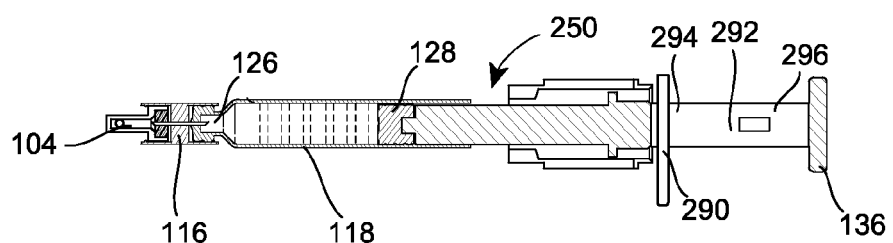
FIG. 16 is a cross-sectional view similar to FIG. 15, with the plunger shaft assembly withdrawn in the direction opposite the medication port to draw fluid from the first container into the second container.
Figure 17:
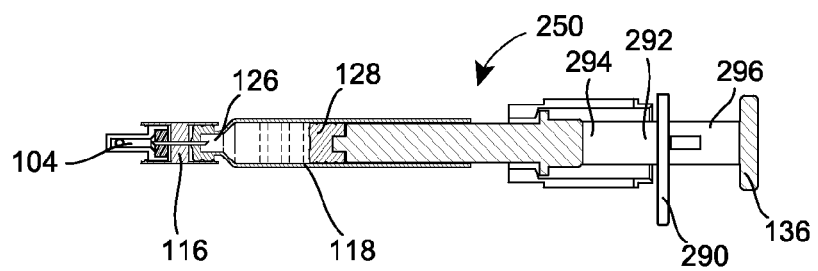
FIG. 17 is a cross-sectional view similar to FIG. 15, with the plunger shaft again advanced into the second container in the direction of the medication port to eject the contents of the second container into the first container.
Figure 18:
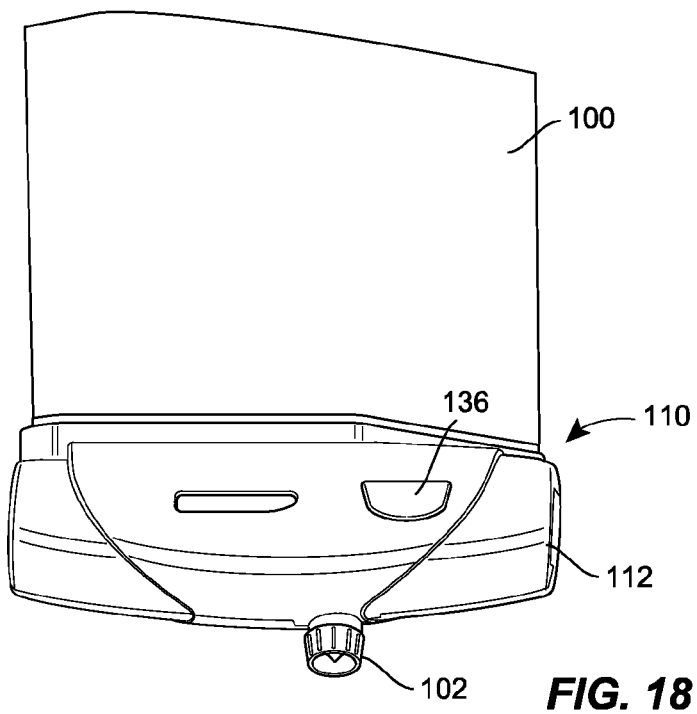
FIG. 18 is a perspective view of a third embodiment of a container system according to the present disclosure.

Further force may be applied to the trigger 136, and the shaft assembly 250 will continued to move to the left, as illustrated in FIG. 15. With the force thus applied, the further movement of the second container 118 will cause the first sharp end 122 of the cannula 120 to puncture and then pass through the plug that defines, in part, the port 104. This will place the cannula 120 in fluid communication with the port 104, and thus place the second container 118 in fluid communication with the port 104, and in fluid communication with the first container 100 via the port 104. To prevent the container 118 from moving back to the right and thus disengaging from the cannula 120, a locking mechanism, in the form of arms or tabs 312 for example, may be provided in certain embodiments, which locking mechanism permits the container 118 to initially move to the left past the locking mechanism and then move inwardly toward the centerline of the container 118 to cooperate with features of the container 118 (e.g., a rightmost edge of the container 118) to limit movement of the container 118 to the right.

At the same time, the tabs 260 will continue to move along the path 270. As the tabs 260 move along the first angled section 274, the axial motion of the shaft assembly 250 and the angled nature of the first angled section 274 causes the collar 264 to rotate about its axis 272. Rotation of the collar 264 about its axis 272 causes the portion of the exterior surface 266 of the collar 264 viewable through the window 252 to change. As a consequence, a new indicia is displayed to the user, suggesting that the user should apply a force to the trigger 136 to the right (e.g., "PULL" with an arrow pointing to the right).

A force applied to the trigger 136 to the right causes the plunger seal 128 to be moved along the second container 118 from a first end to a second end of the container 118. Because the second container 118 is in fluid communication with the first container 100, the movement of the seal 128 to the right causes fluid to be drawn from the first container 100 into the second container 118. If a drug or additive is already in the second container 118, in lyophilized form for example, the fluid drawn from the first container 100 into the second container 118 may be used to reconstitute the material in the second container 118. The delivery device 110 may be shaken to assist in the reconstitution process.

As the force is applied to the trigger 136, the tabs 260 move along the straight section 282 and then the second angled section 276. As the tabs 260 move along the straight section 282, the collar 264 maintains its position relative to the window 252. As the tabs 260 move along the second angled section 276, however, the collar 264 again rotates about its axis 272, causing the portion of the exterior surface 266 of the collar 264 viewable through the window 252 to change. As a consequence, a new indicia is displayed to the user, suggesting that the user should apply a force to the trigger 136 to the left (e.g., "PUSH" with an arrow pointing to the left).

A force applied to the trigger 136 to the left again causes the plunger seal 128 to be moved along the second container 118. This time, however, the plunger seal 128 moves from the second end of the container 118 to the first end. As a consequence, the fluid drawn from the first container 100 and the material initially in the second container 118 (e.g., a lyophilized drug, now reconstituted) is ejected through the connector 116 (and in particular the cannula 120) into the medication port 104, and from the port 104 into the container 100. With the drug, additive, or other material thus introduced into the container 100, the container 100 may be shaken to encourage admixture, and then the administration port 102 may be spike to administer the contents of the container 100 to a patient (e.g., "SPIKE").

As the force is applied to the trigger 136, the tabs 260 move along the third angled section 278. As the tabs 260 do so, the collar 264 rotates about its axis 272 to cause the portion of the exterior surface 266 of the collar 264 viewable through the window 252 to change. As a consequence, a still further indicia is displayed to the user, suggesting that the user may now spike the administration port 102 to administer the contents of the container 100 to the patient.

Having thus described the structure and operation of the embodiment illustrated in FIGS. 8-17, another embodiment of the container system according to the third class of embodiments is illustrated in FIGS. 18-24. As was the case with the embodiment illustrated in FIGS. 1-7, the container system of FIGS. 18-24 includes a first container 100 with an administration port 102 and a medication port 104 (see FIG. 19). The system also includes a delivery device 110 with a housing 112, a connector 116, a second container 118, and a plunger shaft assembly (see also FIG. 19). For purposes of differentiation, this plunger shaft assembly will be referred to as an automated plunger shaft assembly 350.

Figure 19:
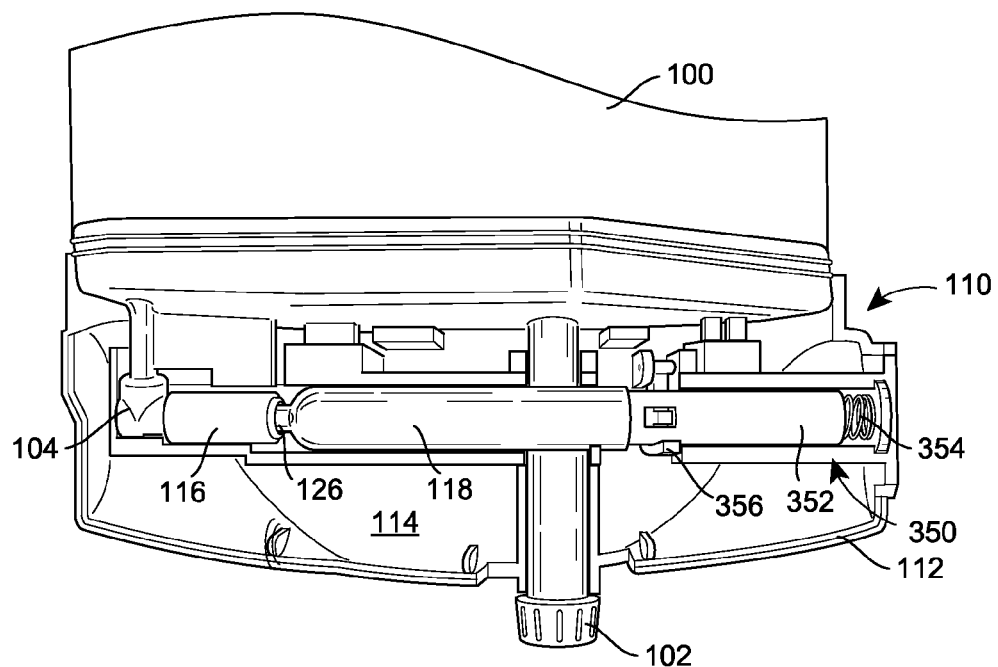
FIG. 19 is a fragmentary, enlarged perspective view of the container system of FIG. 18, with a portion of the housing removed to expose structures of a first container and a delivery device.
Figure 20:
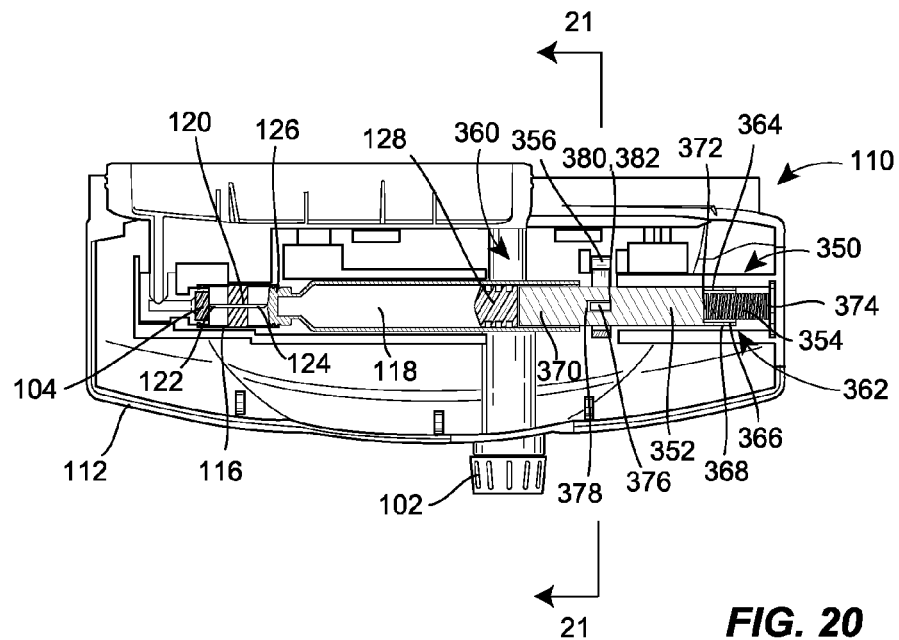
FIG. 20 is a cross-sectional view of the container system of FIG. 18 with an automated plunger shaft assembly in a first state.

As seen in FIGS. 19 and 20, the plunger shaft assembly 350 includes a shaft 352, a biasing element (such as a spring) 354, and a shaft latch (or lock) 356. The biasing element 354 biases the shaft 352 in the direction of the medication port 104, such that the shaft 352 would abut against the second container 118 and apply a force against the second container 118 (particularly the plunger seal 128) to cause the second sharp end 124 of the cannula 120 to puncture the outlet port 126 of the second container 118 (see FIG. 23), the first sharp end 122 of the cannula 120 to puncture the medication port 104 (see also FIG. 23), and eventually the plunger seal 128 to move along the container 118 to force the contents out of the second container 118 through the medication port 104 into the first container 100 (see FIG. 24). However, the shaft latch 356 substantially limits the movement of the shaft 352 to prevent this sequence of events until the shaft latch 356 is selectively moved (rotated, as illustrated) from its locked state (see FIG. 21) to its unlocked state (see FIG. 22).

Now with reference to FIG. 20, it will be recognized that the shaft 352 includes a first end 360 and a second end 362. The shaft 352 has a section with a hollow cylindrical shape between the first and second ends 360, 362 defined by a wall 364 that has an annular cross-section, with an inner surface 366 and an outer surface 368. The first end 360 of the hollow shaft 352 is closed by a plug 370, while the second end 362 of the hollow shaft 352 is open.

The biasing element 354 has a first end 372 and a second end 374. The spring 354 is disposed through the open end 362 of the shaft 352, with the first end 372 of the spring 354 abutting the inner surface of the plug 370. In its compressed state, the spring 354 preferably does not contact the inner surface 366 of the wall 364 of the shaft 352. The second end 374 of the spring 354 may abut an inner surface of the housing 112 or a support structure attached to the inner surface of the housing 112. As noted above, the spring 354 applies a biasing force in the direction of the medication port 104, which biasing force is transmitted through the first end 360 of the shaft 352 to the second container 118 through the plunger seal 128.

Figure 21:
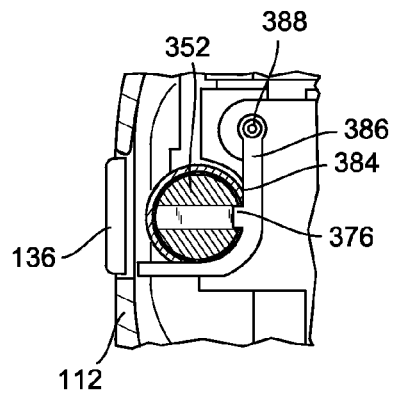
FIG. 21 is a cross-sectional view taken along line 21-21 of the plunger shaft latch in a first, locked state.
Figure 22:
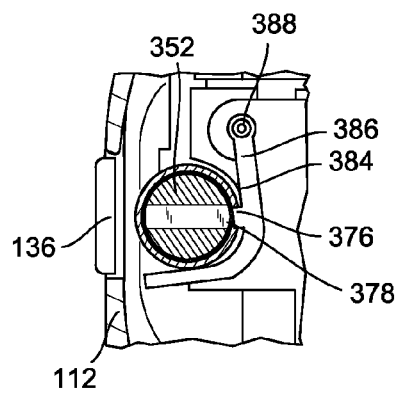
FIG. 22 is a cross-sectional view taken along line 21-21 of the plunger shaft latch in a second, unlocked or operational state.
Figure 23:
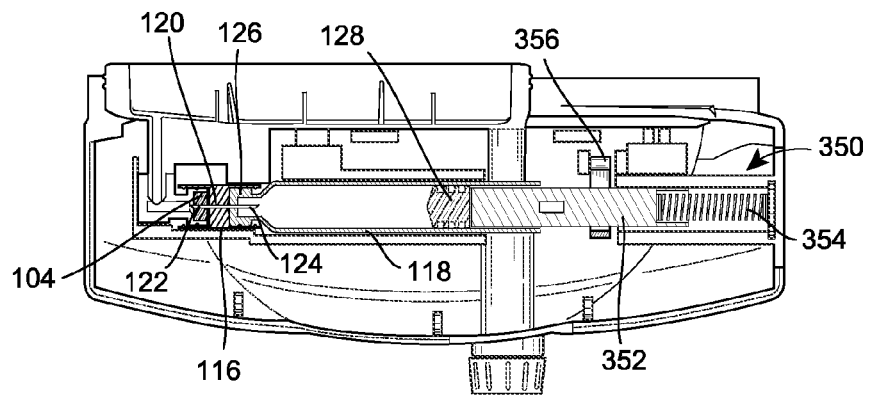
FIG. 23 is a cross-sectional view of the container system of FIG. 18 with the automated plunger shaft assembly advanced in the direction of a medication port to open fluid communication between a connector, a medication port of the first container, and a second container.
Figure 24:
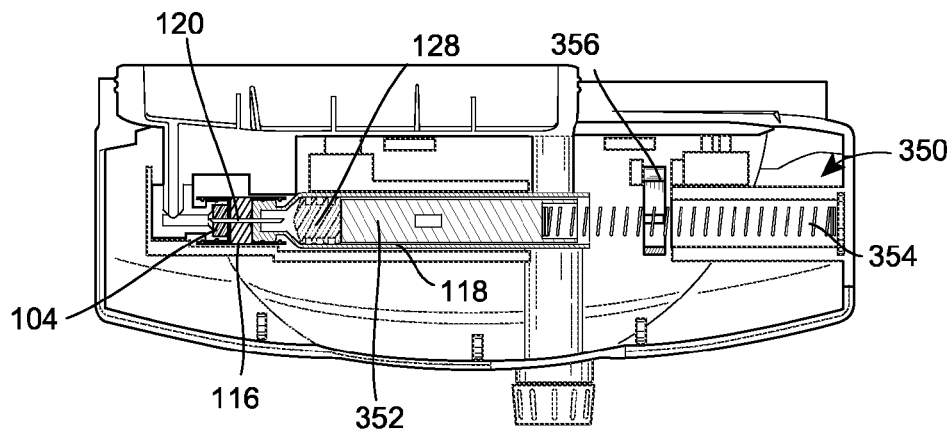
FIG. 24 is a cross-sectional view of the container system of FIG. 18 with the plunger advanced in the direction of the medication port to deliver fluid from the second container to the first container.

The movement of the biased shaft 354 in the direction of the medication port 104 along the axis of the second container 118 is substantially and selectively limited by the shaft latch 356. In particular, the shaft latch 356 cooperates with the shaft 352 such that when the latch 356 and the shaft 352 are in a locked storage state, surfaces of the latch 356 and the shaft 352 limits motion of the shaft 352, while in an unlocked operational state, these surfaces are separated or spaced from each other, permitting the motion of the shaft 352 according to the biasing action of the spring 354. As illustrated in FIGS. 20-22, the latch 356 may have a tab 376 that is disposed within a slot 378 formed in the shaft 352. A surface 380 at the right end of the tab 376 (as oriented in FIG. 20) may abut a surface 382 at the right end of the slot 378 to limit or prevent motion of the shaft 352 in the direction of the medication port 104. The slot 378 depends through the shaft 352 (see FIGS. 19, 21, 22), although this is not required according all embodiments of the present disclosure.

The tab 376 is arranged on an inner surface 384 of a curved lever 386 as best seen in FIGS. 21 and 22. The lever 386 is curved so that the lever 386 is disposed about the second container 118 to permit it to be connected or coupled to a trigger 136 disposed on an outer surface of the housing 112. A force may be applied to the trigger 136, and as a consequence to the lever 386, to move the lever 386 and thus move the surfaces of the tab 376 and the slot 378 out of engagement (compare FIGS. 21 and 22). Once the tab 376 and the slot 378 are out of engagement, the biasing element 354 applies a force to the shaft 352, which is applied to the plunger seal 128. Because the second container 118 is sealed at this point, the outlet port 126 of the second container 118 is urged against the second sharp end 124, and sequentially or concurrently the first sharp end 122 is urged against the medication port 104. As a consequence, fluid communication is established between the outlet port 126 and the medication port 104. Fluid can then pass from the second container 118 to the first container 100.

According to the illustrated embodiment, the lever 386 is attached at a pivot 388 to the housing 112 (see FIGS. 21 and 22). Consequently, when the trigger 136 is depressed in the direction of the housing 112, the lever 386 rotates about the pivot 388 to move the surfaces of the tab 376 and the slot 378 out of engagement with each other. Once the tab 376 has been moved out of engagement with the slot 378, the lever 386 will remain rotated out of its locked storage state because of abutment of the tab 376 with the outer surface 368 of the wall 364. It will be recognized that this is merely an exemplary embodiment of a structure for the latch 354, and other structures may be designed to maintain the tab 376 of the latch 354 in engagement and move the tab 376 out of engagement with the slot 378.

The operation of the device is now discussed with reference to FIGS. 20-24. In a first, storage state illustrated in FIG. 20, the tab 376 is received within the slot 378. At this point, a force may be applied to the trigger 136 to urge the shaft latch 356 to rotate about the pivot 388, thereby moving the shaft latch 356 out of engagement with the shaft 352. In particular, the lever 386 is moved (rotated) about the pivot 388 so that the tab 376 is moved out of engagement with the slot 378, thereby separating the surfaces 380, 382 of the tab 376 and the slot 378 that abut to limit or prevent motion of the shaft 352. See FIGS. 20-22. As the shaft 352 of the automated shaft assembly 350 moves in the direction of the medication port 104 according to the force applied by the spring 354, the second container 118 is also moved to the left. See FIG. 23. In fact, the outlet port 126 is moved in the direction of the connector 116 until the second sharp end 124 of the cannula 120 punctures and then passes through the outlet port 126. The cannula 120 is thus placed in fluid communication with the second container 118. Further motion eventually causes the outlet port 126 of the second container 118 to abut against an interior surface of the connector 116, at which point further motion of the second container 118 may translate into motion of the connector 116 as well.

Motion of the second container 118 and the connector 116 to the left causes the first sharp end 122 of the cannula 120 to abut against a plug that defines, in part, the medication port 104 of the first container 100. With further axial motion along the common axis of the port 104, connector 116, second container 118 and automated assembly 350, the first sharp end 122 punctures and passes through the plug of the medication port 104, thus placing the cannula 120 in fluid communication with the medication port 104. As a further consequence, the second container 118 is in fluid communication with the medication port 104 via the connector 116 (and in particular via the cannula 120).

With still further application of force by the spring 354, the adjustable assembly 150 causes the plunger seal 128 to move along the second container 118 in the direction of a first end of the container 118 from a second end of the container 118. Compare FIGS. 23 and 24. The motion of the plunger seal 128 to the left causes the contents of the second container 118 to be ejected from the second container 118 into the cannula 120, and through the cannula 120 into the medication port 104 and ultimately the first container 100. The movement of the plunger seal 128 may be visualized through a window in the housing 112 (see FIG. 18), permitting confirmation of the delivery and dose of the material from the second container 118 to the first container 100.

Having thus described the structure and operation of the embodiment illustrated in FIGS. 18-24, another embodiment of the container system according to the fourth class of embodiments, wherein reconstitution capability is provided, is illustrated in FIGS. 25-35. As was the case with the preceding embodiments, the container system of FIGS. 25-35 includes a first container 100 with an administration port 102 and a medication port 104 (see FIG. 26). The system also includes a delivery device 110 with a housing 112, and a second container 118 with an associated (first) plunger shaft assembly (see also FIG. 26). However, this delivery device 110 has a third container with an associated (second) plunger shaft assembly. Moreover, the connector of this delivery device selectively couples the first, second and third containers in fluid communication.

In general terms, the connector has at least one cannula defining a first sharp end aligned with the medication port, a second sharp end, and a third sharp end. The delivery device includes a second container having an outlet port aligned with the second sharp end of the at least one cannula and a plunger seal moveable within the second container to force contents of the second container through the outlet port, and an associated (first) plunger shaft assembly having a first end that abuts the plunger seal of the second container and a second end connected to an associated trigger. The delivery device also includes a third container having an outlet port aligned with the third sharp end of the at least one cannula and a plunger seal moveable within the third container to force contents of the third container through the outlet port, and an associated (second) plunger shaft assembly having a first end that abuts the plunger seal of the third container and a second end connected to an associated trigger.

The connector has a first state wherein the connector couples the second and third containers in fluid communication, and a second state wherein the connector couples the first and second containers in fluid communication. Further, the second plunger shaft assembly has a first storage state, and a second operative state wherein the second plunger shaft assembly applies a force to the plunger seal within the third container to force the contents or a portion of the contents of the third container into the second container upon activation of the associated trigger with the connector in the first state. Additionally, the first plunger shaft assembly has a first storage state, and a second operative state wherein the first plunger shaft assembly applies a force to the plunger seal within the second container to force the contents or a portion of the contents of the second container into the first container upon activation of the associated trigger with the connector in the second state.

As illustrated and explained in greater detail below, the plunger shaft assembly associated with the second container 118 may be an adjustable plunger shaft assembly. In fact, the second container 118 and associated adjustable plunger shaft assembly have structural and operational similarities to the embodiment of FIGS. 1-7. Further, the plunger shaft assembly associated with the third container may be an automated plunger shaft assembly, and the illustrated third container and associated automated plunger shaft assembly have structural and operational similarities to the embodiment of FIGS. 18-24.

According to the illustrated embodiment, a diluent contained in the third container is transferred to the second container to reconstitute a lyophilized product, for example. The transfer may occur in an automated fashion with manipulation of the trigger associated with the automated plunger shaft assembly. Once the diluent is transferred, the user may shake the device to enhance reconstitution process. The reconstituted product or some portion thereof then may be transferred to the first container through manipulation of the trigger associated with the adjustable plunger shaft assembly.

Of course, the illustrated embodiment is simply one example according to this class of embodiments. For example, instead of a second container and associated adjustable plunger shaft assembly, a second container and associated automated plunger shaft assembly may be provided so that all of the reconstituted product is delivered to the first container. Such an embodiment may be used where it is not preferable to permit the user to select the amount of reconstituted product to deliver to the first container 100, for example. Moreover, while the delivery device 110 includes second and third containers, the delivery device may include two or more containers.

Figure 25:
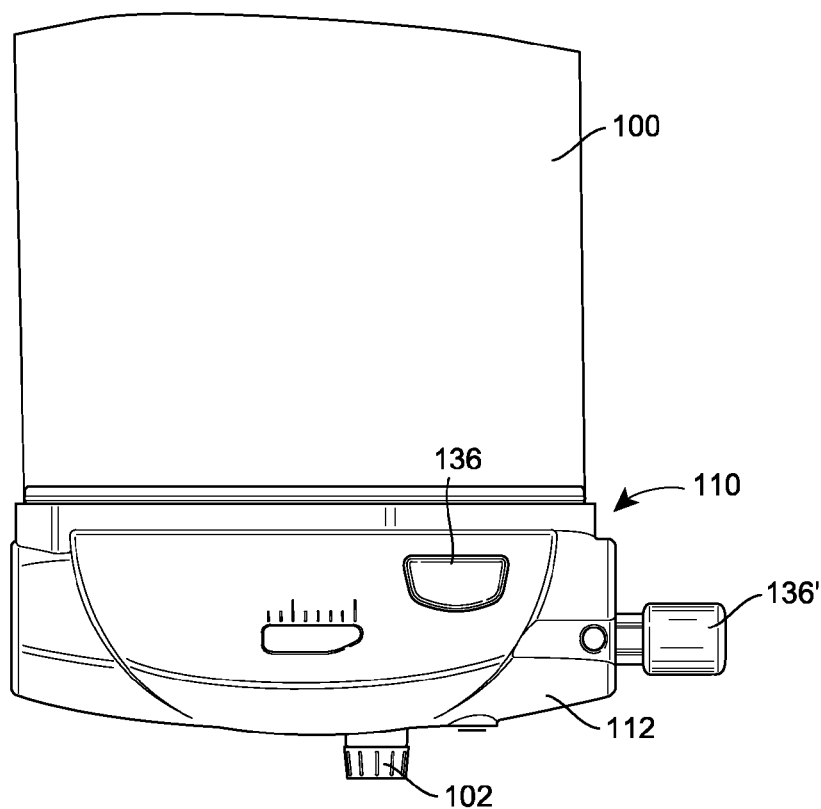
FIG. 25 is a perspective view of a fourth embodiment of a container system according to the present disclosure.

The illustrated embodiment is now discussed with reference to FIGS. 25-35 With reference to FIG. 26, it will be recognized that the delivery device 110 includes a third container 400 and an associated automated plunger shaft assembly 410 (associated with trigger 136 illustrated in FIG. 25). In particular, the plunger shaft assembly 402 includes a shaft 412, a biasing element (such as a spring) 414, and a shaft latch (or lock) 416.

Figure 26:
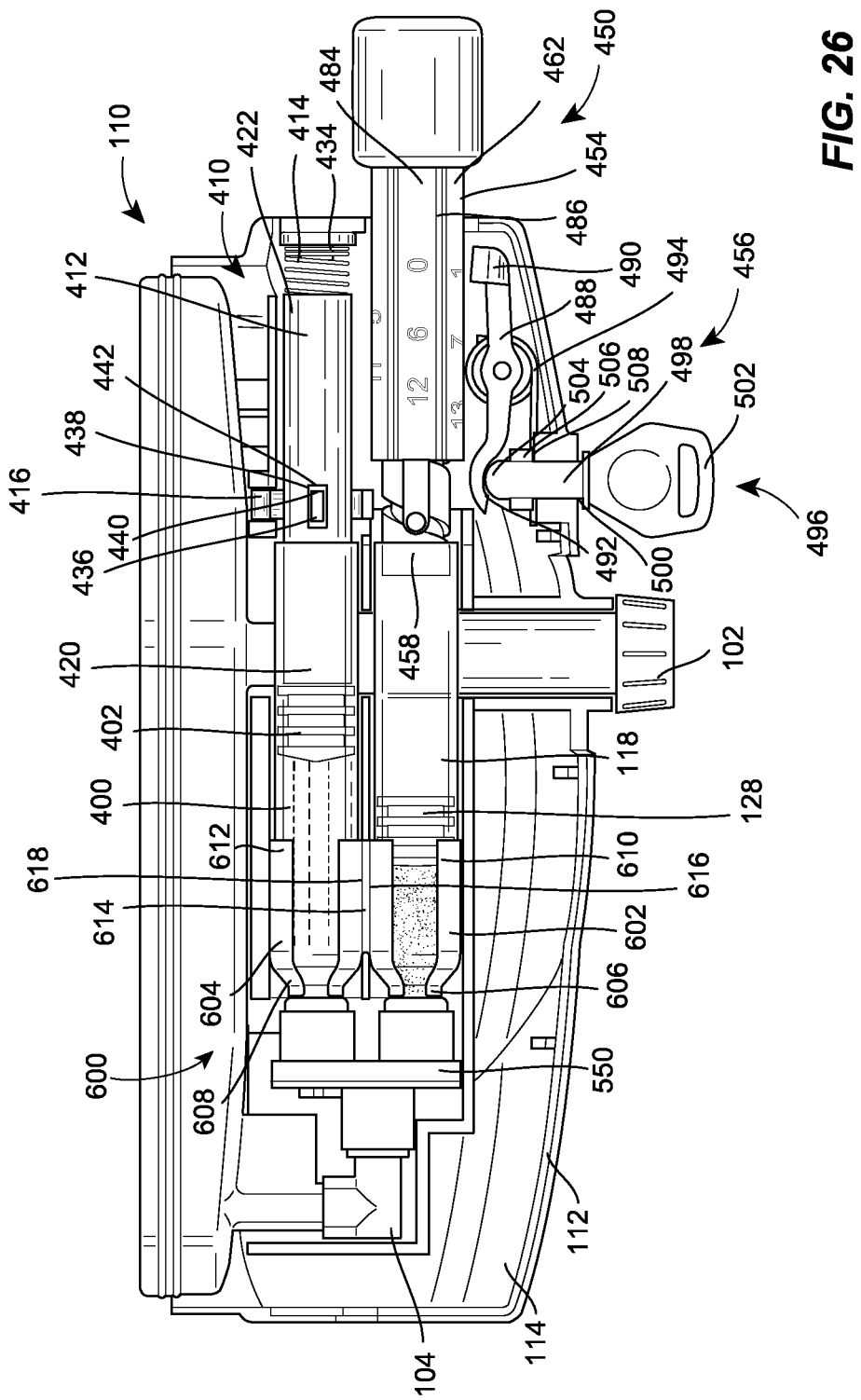
FIG. 26 is a fragmentary, enlarged perspective view of the container system of FIG. 25, with a portion of the housing removed to expose structures of a first container and a delivery device.
Figure 29:
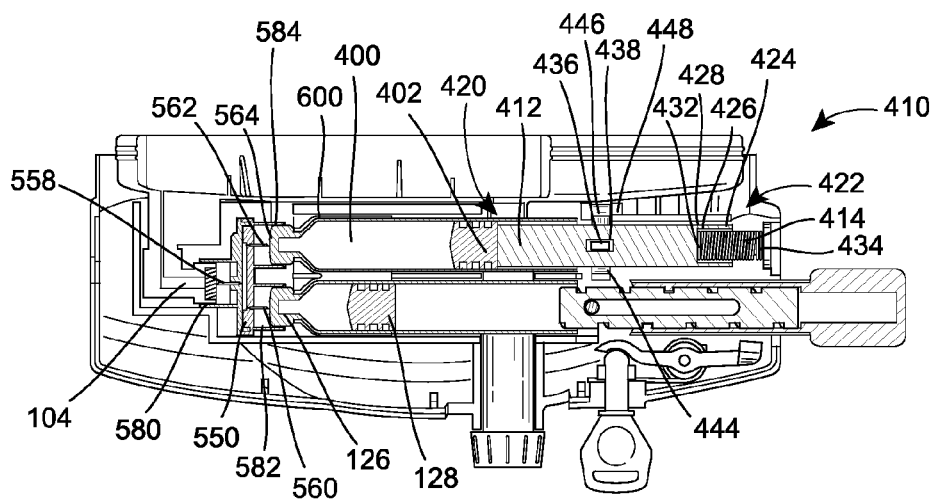
FIG. 29 is a cross-sectional view of the container system of FIG. 25 with an automated plunger shaft assembly associated with the third (diluent) container in a first state.
Figure 30:
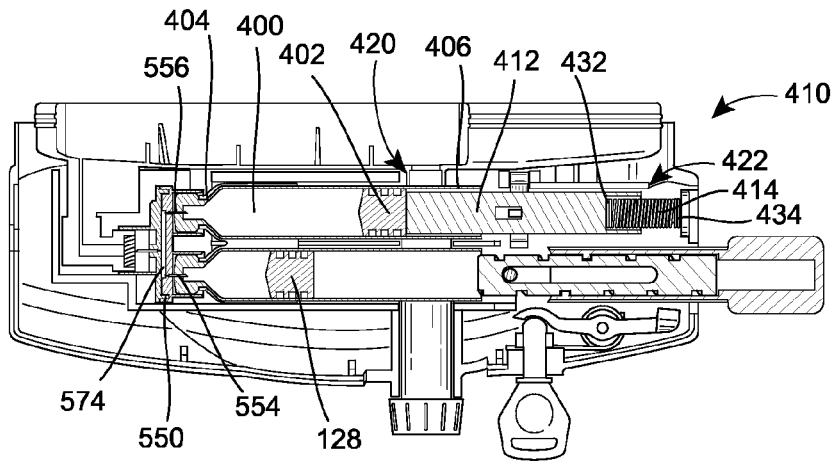
FIG. 30 is a cross-sectional view of the container system of FIG. 25 with the automated plunger shaft assembly advanced in the direction of the connector to open fluid communication between the connector, the second container, and third (diluent) container.
Figure 31:
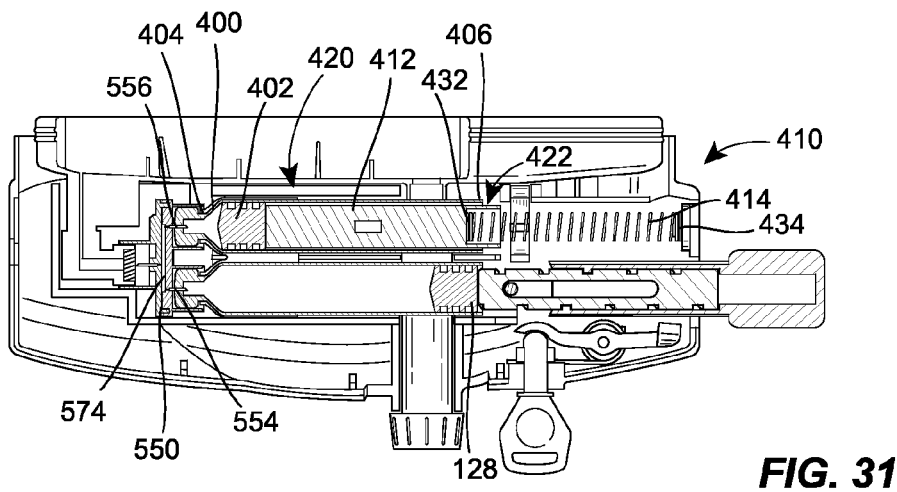
FIG. 31 is a cross-sectional view of the container system of FIG. 25 with the plunger advanced in the direction of the connector to deliver fluid from third (diluent) container to the second container.

With reference to FIGS. 26 and 29, the shaft 412 includes a first end 420 and a second end 422. As seen in FIG. 29, the shaft 412 has a hollow cylindrical shape between the first and second ends 420, 422 defined by a wall 424 that has an annular cross-section, with an inner surface 426 and an outer surface 428. The first end 420 of the hollow shaft 412 is closed by a plug 430, while the second end 422 of the hollow shaft 412 is open.

The biasing element (e.g., spring) 414 has a first end 432 and a second end 434. The spring 414 is disposed through the open end 422 of the shaft 412, with the first end 432 of the spring 414 abutting the inner surface of the plug 430. The second end 434 of the spring 414 may abut an inner surface of the housing 112 or an support structure attached to the inner surface of the housing 112.

The latch 416 may have a tab 436 that is received within a slot 438 formed in shaft 412. A surface 440 at the right end of the tab 436 may abut a surface 442 at the right end of the slot 438 to limit or prevent motion of the shaft 352 in the direction of the medication port 104 (see FIG. 26). The tab 436 is arranged on an inner surface 444 of a curved lever 446 (see FIG. 29). A force may be applied to the trigger 136, and as a consequence to the lever 444, to move the lever 444 to move the surfaces 440, 442 of the tab 436 and the slot 438 out of engagement. According to the illustrated embodiment, the lever 446 is attached at a pivot 448 to the housing 112.

Figure 32:
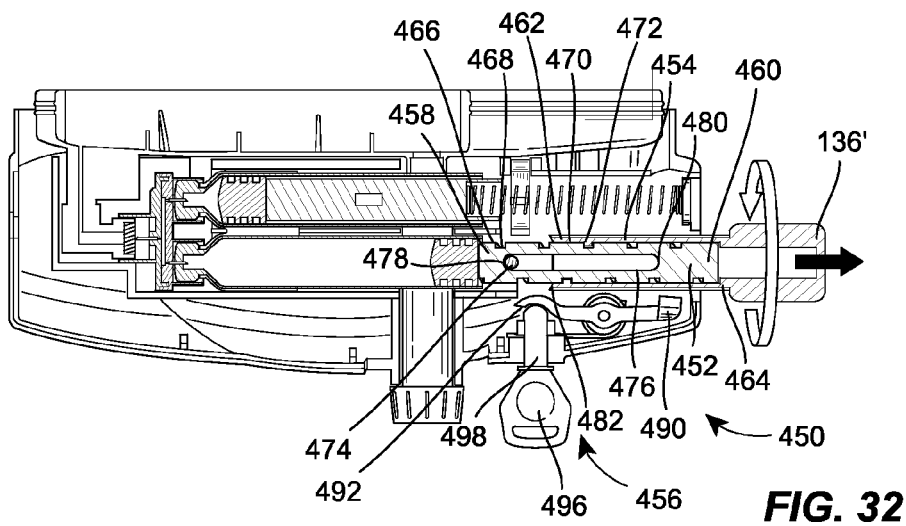
FIG. 32 is a cross-sectional view of the container system of FIG. 25 with the adjustable plunger shaft assembly in a (non-zero-dose) state, and the lock in the unlocked state.
Figure 33:
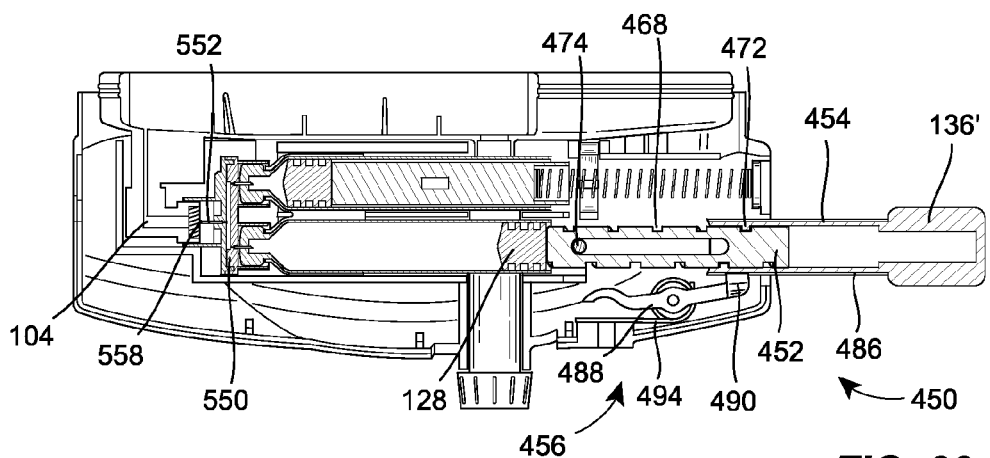
FIG. 33 is a cross-sectional view of the container system of FIG. 25 with the adjustable plunger shaft assembly in the (non-zero-dose) state, and the lock in a locked state.

Now with reference to FIGS. 26 and 32, the second container 118 has an associated adjustable plunger shaft assembly 450 with first and second shaft sections 452, 454 and a lock 456 connected to the first and second shaft sections 452, 454. The lock 456 has a first state that permits relative motion between the first and second shaft sections 452, 454. The lock 456 also has a second state that limits relative motion between the first and second shaft sections 452, 454.

As best seen in FIG. 32, the first shaft section 452 may be a solid shaft with a first end 458 and a second end 460. The second shaft section 454 may be a hollow tube with a first end 462 and a second end 464. The second end 460 of the solid shaft 452 and the first end 462 of the hollow tube 454 may threadedly engage each other to permit relative motion thereof. For example, the shaft 452 may have an exterior surface 466 with a groove 468 formed therein, and the tube 454 may have an interior surface 470 with a thread 472 depending therefrom. It will be recognized that other mechanisms may be provided to provide relative motion between the first and second shaft section 452, 454.

As illustrated, the adjustable assembly 450 may also include a pin 474 disposed in a slot 476 formed in the solid shaft 452. The pin 474 is secured at its ends to the housing 112, and thus is immovable relative to the housing 112. Despite this, the pin 474 may be described herein as moving relative to features of the adjustable assembly 450, even though the adjustable assembly 450 is, in fact, moving relative to the housing 112 and the pin 474.

The pin 474 cooperates with the slot 476 to resist rotational motion of the solid shaft 452. The pin 474 is generally moveable in the slot 476 between ends 478, 480 of the slot 476, further limited by the general spatial relationship between the shaft 452 and the tube 454. Specifically, the tube 454 has an edge 482 that may overlie the slot 476; the exact position of the edge 482 relative to the slot 476 (particularly, relative to the first and second ends 478, 480 of the slot 476) determines the extent of the relative motion between the shaft 452 and tube 454. The pin 474 is thus moveable relative to the ends 478, 480 unless the edge 482 is disposed between the ends 478, 480, in which case the pin 474 is moveable between the end 478 and the edge 482, although the pin 474 may or may not come in contact with the ends 478, 480 or edge 482. The extent to which the pin 474 is moveable between the ends 478, 480 determines the dose of the contents of the second container 118 delivered to the first container 100.

The spatial relationship between the first and second shaft sections 452, 454 may be limited, or even fixed, through the lock 456. As illustrated, the tube 454 has an exterior surface 484 with a plurality of longitudinal grooves 486 (see FIG. 26). The lock 456 engages the longitudinal grooves 486 to limit relative motion between the solid shaft 452 and hollow tube 454. Specifically, the lock 456 includes a lever 488 having a first end 490 and a second end 492. The lock 456 also includes a spring 494 that biases the first end 490 toward one of the plurality of longitudinal grooves 486. The lock 456 also includes a key 496 that abuts the second end 492 of the lever 488 when inserted into the lock 456 to space the first end 490 of the lever 488 from the plurality of longitudinal grooves 486.

In particular, the key 496 has a shaft 498 is disposed through an opening 500 in housing 112 of the delivery device 110, and a head 502 that is manipulatable by the user. The shaft 498 has an end 504 with a pair of supports 506 spaced from the end 504. The supports 506 abut against an inner surface or shoulder 508 formed at an inner end of the opening 500 in the housing 112. The cooperation of the supports 506 with the shoulder 508 ensures that the shaft 498 cooperates with the second end 492 of the lever 488 to space the first end 490 of the lever from the grooves 486 to limit the cooperation of the end 490 and the grooves 486 (i.e., to prevent the first end 490 of the lever 488 from being received in the grooves 486). To accommodate the supports 506, which depend radially outwardly from the shaft 498, the opening 500 may have a complementary cross-section.

The delivery device 110 according to this embodiment may also include a connector 550 (which may also be referred to as a fluid path connector), that connects the second container 118 to the first container 100. See FIGS. 26 and 27. Differing from the connectors described above, the connector 550 also is used to connect the third connector 400 to the second container 118. As illustrated, the connector 550 may include multiple cannulas 552, 554, 556 each with a sharp end 558, 560, 562. The sharp end 558 of the cannula 552 is aligned with the medication port 104, the sharp end 560 of the cannula 554 is aligned with the outlet port 126 of the second container, and the sharp end 562 of the cannula 556 is aligned with an outlet port 564 of the cannula 556. See FIG. 29.

Figure 27:
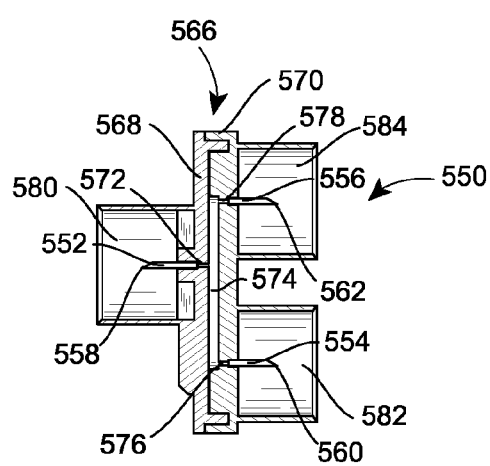
FIG. 27 is a cross-sectional of the connector used in the fourth embodiment of the container system of FIG. 25.

As illustrated in FIG. 27, the connector 550 also includes a housing 566 to which the cannulas 552, 554, 556 are attached and that defines the flow paths between the cannulas 552, 554, 556. According to the illustrated embodiment, the housing 566 includes a first housing section 568 to which the cannula 552 is attached, and a second housing section 570 to which the cannulas 554, 556 is attached. The first housing 568 includes a first passage 572 that is in fluid communication with a groove 574 that is formed on one of the first and second housing sections 568, 570 (as illustrated, in the second housing section 570). The groove 574 is in fluid communication with a second passage 576 and a third passage 578, which passages are in communication with the cannulas 554, 556, respectively.

In addition, the connector 550 includes a first collar or cylindrical wall 580 depends in the direction of the medication port 104, a second collar or cylindrical wall 582 depends in the direction of the container 118, and a third collar or cylindrical wall 584 depends in the direction of the container 400. As such, the first collar 580 is disposed about the first sharp end 558, the second collar 582 is disposed about the second sharp end 560, and the third collar 584 is disposed about the third sharp end 562. As illustrated, the collars 580, 582, 584 have approximately the same inner and outer diameter, although this need not be the case according to all embodiments.

In certain embodiments, the medication port 104 may be disposed within the first collar 580, an end of the container 118 (e.g., outlet port 126) may be disposed within the second collar 582, and an end of the container 400 (e.g., outlet port 564) may be disposed within the third collar 584 so as to form a sterile barrier at either end of the connector 550, thus defining a sterile environment within the interior of the connector 116 (see FIG. 29). For example, the medication port 104 may be bonded to the first collar 580 with the sharp end 558 of the cannula 552 partially disposed in the plug of the medication port 104, and the ends of the containers 118, 400 and the collar 582, 584 fitted within particular tolerances so as to maintain sterility. It will be recognized that other mechanism and methods for forming a sterile barrier at either end of the connector 550 may be used as well.

Figure 28:
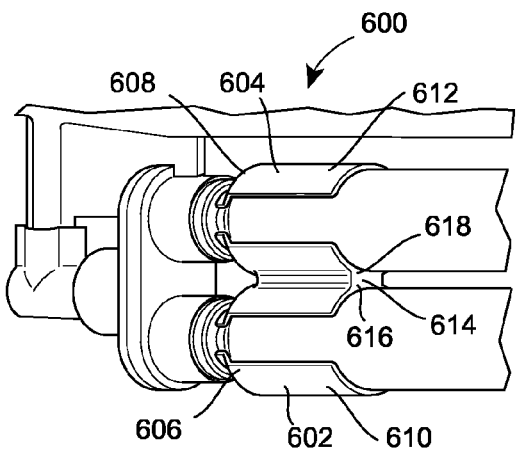
FIG. 28 is a fragmentary, enlarged view of a fastener used to connect a second container and a third (diluent) container.

The delivery device 110 according to the embodiment of FIGS. 25-35 also includes a fastener 600 that secures the second container 118 to the third container 400 such that the second container 118 and the third container 400 may move together within the housing 112. As best seen in FIGS. 26 and 28, the fastener 600 includes two cylindrical barrels 602, 604, each of which has a first open end 606, 608 and a second open end 610, 612, the first open ends 610, 612 being of reduced diameter relative to the second open ends 610, 612 to seat the containers 118, 400 within the barrels 602, 604. The barrels 602, 604 may be connected by a bridge 614, with the first end 616 of the bridge 614 attached to the first barrel 602 and the second end 618 of the bridge 614 attached to the second barrel 604. It will be recognized that the second container 118 and the third container 400 may be connected by other mechanisms than the fastener 600 illustrated in FIGS. 26 and 28; for example, the containers 118, 400 may be attached together simply by attaching the containers 118, 400 using an adhesive as the fastener.

The operation of the illustrated device is now discussed with reference to FIGS. 29-35. The order of operation is as follows: the diluent is delivered from the third container 400 to the second container 118, the lyophilized product is reconstituted, and then the reconstituted product is delivered from the second container 118 to the first container 100. To achieve this general order of operation, it is necessary to dispose the second and third containers 118, 400 in fluid communication with the connector 550, while the connector 550 is not in fluid communication with the medication port 104 (e.g., the sharp end 558 of the cannula 552 is not disposed through the plug of the medication port 104). After the second and third containers 118, 400 are in fluid communication with the connector 550, the fluid is delivered from the third container 400 to the second container 118. After the fluid is delivered to the second container 118, the connector 550 is placed in fluid communication with the medication port 104, and the fluid from the second container 118 is delivered to the first container 100.

Thus, in a first storage state illustrated in FIG. 29, the tab 436 is received within the slot 438. At this point, a force may be applied to the trigger 136 to urge the shaft latch 416 to rotate about the pivot 448, thereby moving the shaft latch 416 out of engagement with the shaft 412. In particular, the lever 444 is moved (rotated) about the pivot 448 so that the tab 436 is moved out of engagement with the slot 438, thereby separating the surfaces 440, 442 of the tab 436 and the slot 438 (see FIG. 26) that abut to limit or prevent motion of the shaft 412. As the automated assembly 410 moves to the left according to the force applied by the spring 414, the third container 400 is also moved to the left. By virtue of the fastener 600, the second container 118 also moves to the left.

In particular, the outlet ports 126, 564 are moved in the direction of the connector 550 until the sharp ends 560, 562 of the cannulas 554, 556 puncture and then pass through the outlet port 126, 564. See FIG. 30. The cannulas 554, 556 are thus placed in fluid communication with the second and third containers 118, 400. As the cannulas 554, 556 are also in communication with groove 574 (see FIG. 27), the second and third containers 118, 400 are in fluid communication with each other.

With still further application of force by the spring 414, the automated assembly 410 causes a plunger seal 402 to move along the third container 400 in the direction of a first end 404 of the container 400 from a second end 406 of the container 400. See FIGS. 29-31. The motion of the plunger seal 402 to the left causes the contents of the third container 400 to be ejected from the third container 400 into the cannula 554, through the groove 574, into the cannula 556, and into the second container 118. See FIG. 31. This may also cause the plunger seal 128 in the second container 118 to move to the right. The delivery device 110 may then be agitated to reconstitute the product.

Having reconstituted the product, the delivery of the product from the container 118 to the container 100 may be discussed relative to FIGS. 32-35. With the key 496 received within the opening 500 in the housing 112 to place the lock 456 in an unlocked state, the two sections 452, 454 of the adjustable assembly 450 may be disposed in a first, zero-dose state. See FIG. 32. Because the lock 456 is unlocked, the two sections 452, 454 of the adjustable assembly 450 may be moved relative to each other. However, with the adjustable assembly 450 in the zero-dose state, actuation of the trigger 136 will cause no motion of the plunger seal 128 such that drug will be dispensed.

In FIG. 32, the second shaft section 454 is moved relative to the first shaft section 452 such that the adjustable assembly 450 is no longer in the zero-dose state. According to the illustrated embodiment, because the first and second shaft sections 452, 454 are connected to each other through a threaded engagement defined by the grooves 468 and the thread 472, the second shaft section 454 is rotated relative to the first shaft section 452 to achieve the relative motion between the two sections 452, 454. As mentioned previously, the pin 474 limits or resists rotational motion of the first shaft section 452 at the same time. In addition, the second shaft section 454 may have indicia (e.g., numbers) disposed on the exterior surface 484 (see FIG. 26) that are viewable through a window in the housing 112 (see FIG. 25) so that a visual indication of the dose associated with the relative position of the first and second shaft sections 452, 454 may be displayed to the user.

Because the shaft 498 of the key 496 abuts against the second end 492 of the lock 456, the first end 490 of the lever 488 is not disposed in the grooves 486 of the second shaft section 454. As a consequence, the second shaft section 454 may be moved relative to the first shaft section 452, as illustrated in FIG. 32. However, when the first and second shaft sections 452, 454 of the adjustable assembly 450 have been adjusted to provide the desired dose, the healthcare profession (e.g., a pharmacist or pharmacy employee) removes the key 496 from the lock 456 (see FIG. 33). As a consequence, the biasing force provided by the spring 494 causes the first end 490 of the lever 488 to be urged toward the grooves 486. With the first end 490 disposed in one of the grooves 486, the movement of the second shaft section 454 about its longitudinal axis is resisted or limited.

Figure 34:
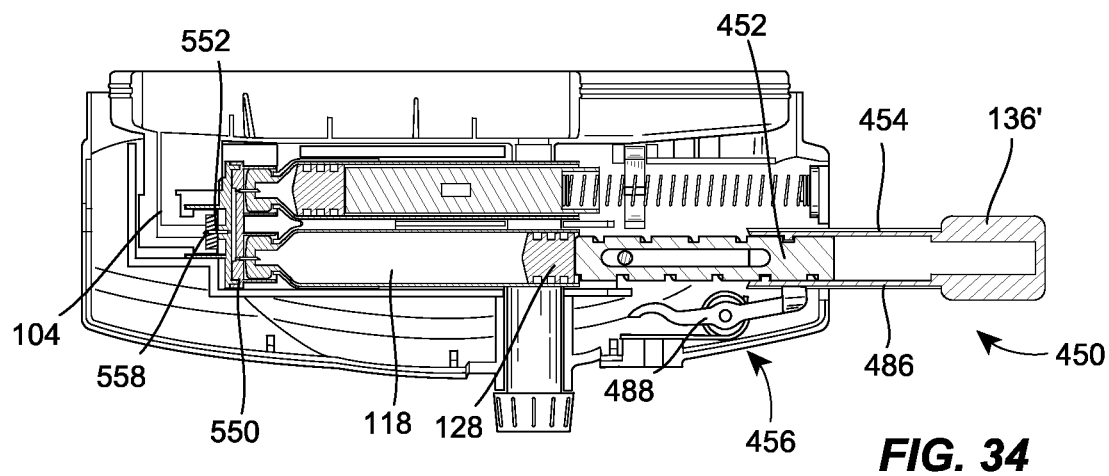
FIG. 34 is a cross-sectional view of the container system of FIG. 25 with the adjustable plunger shaft assembly advanced in the direction of a medication port to open fluid communication between the connector and the medication port of the first container.
Figure 35:
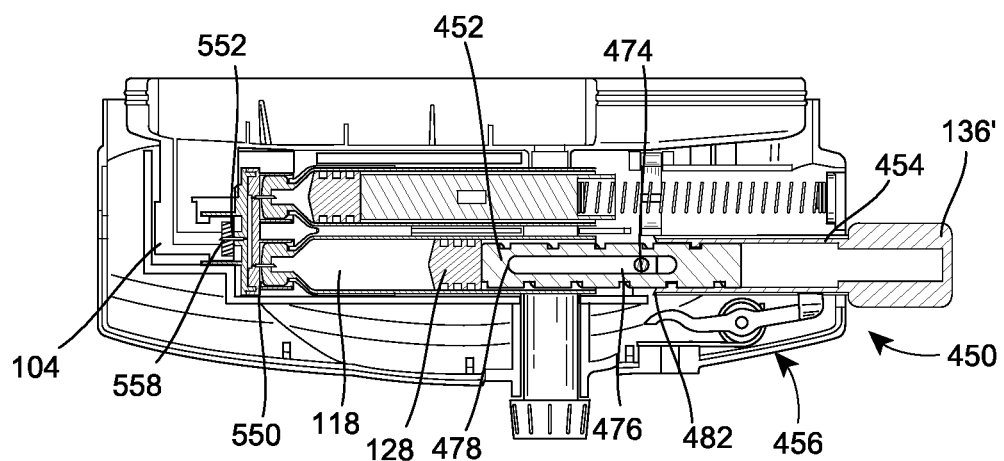
FIG. 35 is a cross-sectional view of the container system of FIG. 25 with the adjustable plunger shaft assembly advanced in the direction of the medication port to deliver fluid from the second container to the first container.

At this point, a force may be applied to the trigger 136' to urge the adjustable assembly 450 to the left, as illustrated in FIG. 34. While the cooperation of the lever 488 and the grooves 486 resists rotational motion of the second shaft section 454, the axial movement of the second shaft section 454 (and the remainder of the adjustable assembly 450) is not resisted by the grooves 486 and the lever 488. As the adjustable assembly 450 is moved to the left, the second container 118 is also moved to the left. With further motion, the first sharp end 558 passes through the plug of the medication port 104, thus placing the cannula 552 in fluid communication with the medication port 104. As a further consequence, the second container 118 is in fluid communication with the medication port 104 via the connector 550 (and in particular via the cannula 552). See FIG. 34.

With still further application of force to the trigger 136' to the left, the adjustable assembly 450 causes the plunger seal to move along the second container 118 in the direction of a first end of the container 118 from a second end of the container 118. See FIG. 35. The motion of the plunger seal 128 to the left causes the contents of the second container 118 to be ejected from the second container 118 into the cannula 552, and through the cannula 552 into the medication port 104 and ultimately the first container 100. The amount or volume of material (e.g., drug, additive, etc.) ejected from the second container 118 into the first container 100 will depend on the motion of the second shaft section 454 relative to the first shaft section 452, which motion causes the edge 482 of the second shaft section 454 to be moved relative to the first end 478 of the slot 476, thereby determining the relative motion permitted through the cooperation of the pin 474 and the slot 476 (or at least that portion of the slot 476 defined between the end 478 and the edge 482). The movement of the plunger seal may be visualized through a window in the housing 112, permitting confirmation of the delivery and dose of the material from the second container 118 to the first container 100.

According to any of the embodiments of the present disclosure, the delivery device 110 is connected to the first container 100, as mentioned previously. According to the embodiments illustrated, the connection of the delivery device 110 to the first container 100 is achieved in the following manner.

As illustrated, for example, in FIGS. 1 and 2, the first container 100 may include a flexible bag 800 with a first, closed end 802 and a second end 804. The first container 100 may also include a gondola 806 from which the administration port 102 and the medication port 104 depend. The gondola 806 is sealed to the second end of the flexible bag 800 so that the contents of the bag 800 may only exit or enter the bag 800 through the administration port 102 and the medication port 104.

As seen in FIG. 2, the gondola 806 has a plurality of arms 808 that depend from the gondola 806. As illustrated, each of the arms 808 has a hook 810 at a first end 812 of the arms 808, a second end 814 of the arms 808 being attached to (and integrally formed with, as illustrated) the gondola 806. The arms 808, and in particular the hooks 810, abut against and cooperate with a plurality of shelves 816 (see FIG. 3) that depend from an inner surface 818 of the housing 112 (see also FIG. 3). In particular, the shelves 816 are disposed between the hooks 810 and the gondola 806 so as to resist removal of the arms 808 from the housing 112. In this manner, the housing 112 may be attached to the gondola 806.

The housing 112 and the first container 100 may also cooperate in other manners, so as to attach or associate the first container 100 and the housing 112. For example, as illustrated in FIGS. 2 and 3, the housing 112 may have channels 820, 822 defined on the inner surface 818 of the housing 112 to position and secure the elements of the first container 100 within the housing 112. For example, the channel 820 accepts the administration port 102, the administration port 102 being disposed through the interior space 114 of the housing 112 and depending therefrom. The channel 822 cooperates with the medication port 104 to align the medication port 104 with the connector 116 and the outlet port 126 of the second container 118. In addition, because the tube that defines the medication port 104 is bent so that an axis 824 of the medication port 104 is perpendicular to the remainder of the tube defining the medication port 104, the cooperation between the medication port 104 and the channel 822 assisting in attaching the housing 112 to the gondola 806.

It is believed that the container system according to the present disclosure may provide one or more advantages, one or more of which may be provided in a particular embodiment of the present disclosure. Initially, the system may provide a mechanism for introducing a material, such as a drug, additive, etc., into a first container from a second container in a system closed with relation to a medication port of the first container. This has certain advantages, in that the possibility of contaminants being introduced into the first container during the delivery of the material to the first container may be limited or reduced. This also as advantages where the material is hazardous to handle, in that direct contact with the hazardous material may be limited or eliminated. Further, the system may reduce or eliminate the likelihood that the drug or additive in the second container will be incorrectly administered to the patient, at least insofar as the drug or additive is associated with the fluid in the first container so as to be inseparable from the first container. Still further, the system may facilitate accurate delivery of the drug or additive where the adjustable shaft assembly is used to determine the dosage delivered to the first container. In addition or in the alternative, the system may guide the operation of the delivery device so as to improve the conditions under which the drug or additive is reconstituted, for example, and then delivered to the first container.

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

For example, a variant of the illustrated embodiments may provide the controlled dosage functionality of the embodiment illustrated in FIGS. 1-7 and the reconstitution functionality of the embodiment illustrated in FIGS. 8-17. According to such an embodiment, a third container may be disposed within the housing, which container holds a diluent used in reconstituting, for example, a lyophilized drug disposed in the second container. The fluid from the third container would be initially introduced into the second container, and used to reconstitute the lyophilized drug. An adjustable assembly may then be used to force some or all of the reconstituted drug from the second container into the first container (or flexible bag).

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

It should be understood other changes and modifications to the presently preferred embodiments described herein would also be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A container system comprising:
a first container assembly having an administration port and a medication port;
a delivery device attached to the first container, and including:
a housing enclosing an interior space, the medication port disposed within the interior space of the housing;
a connector having at least one cannula defining a first sharp end aligned with the medication port and a second sharp end;
a second container having an outlet port aligned with the second sharp end of the at least one cannula and a plunger seal moveable within the second container to force contents of the second container through the port;
a plunger shaft assembly having a first end that abuts the plunger seal and a second end connected to a trigger, wherein:
the connector having a storage state wherein the first end is not in fluid communication with the medication port and the second end is not in fluid communication with the outlet port, and an operational state wherein the first end is in fluid communication with the medication port and the second end is in fluid communication with the outlet port, and wherein:
the medication port comprises a plug and the outlet port comprises a stopper, and
the first sharp end of the connector is not disposed through the plug in the storage state, and is disposed through the plug in the operational state,
the second sharp end of the connector is not disposed through the plug in the storage state, and is disposed through the plug in the operational state.

2. The container system according to claim 1, wherein:
the medication port, the connector and the second container are aligned along a common axis, and the plunger seal is moveable along the common axis.

3. The container system according to claim 1, wherein:
the plunger shaft assembly is adjustable and comprises first and second shaft sections, the first shaft section defining the first end of the plunger shaft assembly and the second shaft section defining the second end of the plunger shaft assembly, the first and second shaft sections moveable relative to each other to vary a distance between the first and second ends;
and further comprising a lock connected to the first and second shaft sections, the lock having a first state that permits relative motion between the first and second shaft sections and a second state that limits relative motion between the first and second shaft sections.

4. The container system according to claim 3, wherein:
the first shaft section comprises a solid shaft with a first end that defines the first end of the plunger shaft assembly and a second end, and the second shaft section comprises a hollow tube with a first end and a second end that defines the second end of the plunger shaft assembly,
the second end of the solid shaft and the first end of the hollow tube threadedly engaging each other to permit relative motion thereof,
the plunger shaft assembly further comprising a pin disposed in a slot formed in the solid shaft to resist rotational motion of the solid shaft.

5. The container system according to claim 4, wherein:
the hollow shaft has an exterior surface with a plurality of longitudinal grooves; and
the lock engages the longitudinal grooves in the second state to limit relative motion between the solid shaft and hollow tube.

6. The container system according to claim 5, wherein
the lock comprising a lever having a first end, a second end, a spring that biases the first end toward one of the plurality of longitudinal grooves, and a key that abuts the second end of the lever when inserted into the lock to space the first end of the lever from the plurality of longitudinal grooves.

7. The container system according to claim 1, wherein the housing has a window, and the plunger shaft assembly comprises a shaft having an exterior surface from which a tab depends and a longitudinal axis, and further comprising:
a state indicator comprising a collar disposed about the plunger shaft assembly, the collar having an exterior surface visible through the window and an interior surface with a path formed therein, the tab received within the path and the path having first, second and third sections each at an angle to the longitudinal axis of the solid shaft, the first and third sections having an opposite slope to the second section.

8. The container system according to claim 7, the plunger shaft assembly comprising a pin disposed in a slot formed in the shaft to resist rotational motion of the shaft about its longitudinal axis.

9. The container system according to claim 7, wherein the path has fourth and fifth sections each parallel to the longitudinal axis, the fourth section disposed prior to the first section and the fifth section disposed between the first and second sections.

10. The container system according to claim 7, further comprising a safety lock connected to the plunger shaft assembly to limit movement of the plunger shaft assembly.

11. The container system according to claim 1, wherein:
the plunger shaft assembly is automated and comprises a shaft and a biasing element coupled to the shaft, the trigger coupled to one of the shaft and the biasing element to selectively control movement of the shaft from a first storage state to a second operational state wherein the shaft applies a force to the plunger seal.

12. The container system according to claim 11, wherein the shaft has a first end abutting the plunger seal and a second end, and the biasing element abuts the second end of the shaft.

13. The container system according to claim 12, wherein the plunger shaft assembly comprises a latch, the latch moveable from a first locked state wherein the latch limits movement of the shaft and a second unlocked state wherein the latch permits movement of the shaft.

14. The container system according to claim 13, wherein the latch has a tab and the shaft has a slot, and the tab is disposed in the slot with the latch in the first locked state, and the tab is spaced from the slot with the latch in the second unlocked state.

15. The container system according to claim 1, wherein:
the first container comprises a flexible bag with a first, closed end and a second end, and a gondola including the administration port and the medication port sealed to the second end of the flexible bag,
the housing attached to the gondola.

16. The container system according to claim 15, wherein:
the second container comprises a cartridge, with the outlet port of the second container including the stopper through which the second sharp end of the connector is disposed to place the connector in fluid communication with the second container.

17. The container system according to claim 1, wherein:
the administration port is disposed through the interior space of the housing to depend from the housing.

18. The container system according to claim 1, wherein:
the second container is disposed within the interior space of the housing.

* * * * *